(12) United States Patent
Bansal et al.

(10) Patent No.: US 10,118,021 B2
(45) Date of Patent: Nov. 6, 2018

(54) CATHETER HAVING AN ACTIVE RETURN-TO-STRAIGHT MECHANISM

(71) Applicant: St. Jude Medical, Cardiology Division, Inc., St. Paul, MN (US)

(72) Inventors: Varun Bansal, Plymouth, MN (US); Michael Bowers, Edina, MN (US); Troy T. Tegg, Elk River, MN (US); David Kim, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 791 days.

(21) Appl. No.: 14/500,809

(22) Filed: Sep. 29, 2014

(65) Prior Publication Data

US 2015/0094654 A1    Apr. 2, 2015

Related U.S. Application Data

(60) Provisional application No. 61/884,897, filed on Sep. 30, 2013.

(51) Int. Cl.
*A61M 25/01* (2006.01)

(52) U.S. Cl.
CPC .... *A61M 25/0147* (2013.01); *A61M 25/0133* (2013.01); *A61M 25/0136* (2013.01); *A61M 2025/0166* (2013.01)

(58) Field of Classification Search
CPC ... A61B 2017/003; A61B 2017/00327; A61M 25/0147; A61M 25/0133; A61M 25/0136; A61M 2025/015; A61M 2025/0161
See application file for complete search history.

(56) References Cited

U.S. PATENT DOCUMENTS

| 4,998,916 A | 3/1991 | Hammerslag et al. |
| 5,037,391 A | 8/1991 | Hammerslag et al. |

(Continued)

FOREIGN PATENT DOCUMENTS

| EP | 0600676 | 6/1994 |
| EP | 0616794 | 9/1994 |

(Continued)

OTHER PUBLICATIONS

PCT/ISA/206 (Invitation to Pay Additional Fees), dated Jan. 22, 2015.

(Continued)

*Primary Examiner* — Emily Schmidt
*Assistant Examiner* — Alexandra Lalonde
(74) *Attorney, Agent, or Firm* — Dykema Gossett PLLC

(57) ABSTRACT

Actuators for steerable medical devices are disclosed that not only deflect or steer a portion of a medical device (e.g., a distal portion of a catheter shaft), but also include mechanisms for actively returning the deflected portion of the medical device to an initial configuration (e.g., straight or substantially straight). These active return-to-straight mechanisms may return a catheter shaft from a deflected configuration to a substantially straight configuration throughout a medical procedure, may employ one or more tension members extending along the catheter shaft, and may comprise a gross return actuator and a fine return actuator. For example, the gross return actuator may be configured to partially reverse the deflection of the distal portion of the catheter; and the fine return actuator may be configured to continue reversing the deflection. The gross return actuator may automatically trigger or actuate (mechanically or electromechanically) the fine return actuator.

15 Claims, 36 Drawing Sheets

(56) References Cited

U.S. PATENT DOCUMENTS

| | | |
|---|---|---|
| 5,108,368 A | 4/1992 | Hammerslag et al. |
| 5,290,229 A | 3/1994 | Paskar |
| 5,308,324 A | 5/1994 | Hammerslag et al. |
| 5,329,923 A | 7/1994 | Lundquist |
| 5,364,352 A | 11/1994 | Cimino et al. |
| 5,383,923 A | 1/1995 | Webster, Jr. |
| 5,389,073 A | 2/1995 | Imran |
| 5,391,147 A | 2/1995 | Imran et al. |
| 5,423,771 A | 6/1995 | Imran |
| 5,656,029 A | 8/1997 | Imran et al. |
| 5,857,997 A | 1/1999 | Cimino et al. |
| 5,861,024 A | 1/1999 | Rashidi |
| 5,876,373 A | 3/1999 | Giba et al. |
| 5,987,344 A * | 11/1999 | West .................. A61N 1/0565 600/373 |
| 6,013,052 A | 1/2000 | Durman et al. |
| 6,198,974 B1 | 3/2001 | Webster, Jr. |
| 6,254,568 B1 | 7/2001 | Ponzi |
| 6,530,913 B1 | 3/2003 | Giba et al. |
| 6,652,506 B2 | 11/2003 | Bowe et al. |
| 7,374,553 B2 | 5/2008 | Koerner et al. |
| 8,162,934 B2 | 4/2012 | Potter |
| 8,177,741 B2 | 5/2012 | Hammack et al. |
| 8,273,016 B2 | 9/2012 | O'Sullivan |
| 8,465,442 B2 | 6/2013 | Freed |
| 2001/0041891 A1 | 11/2001 | Thompson et al. |
| 2005/0187455 A1* | 8/2005 | Rashidi ............. A61B 18/1492 600/374 |
| 2006/0074383 A1* | 4/2006 | Boulais ............... A61B 1/0052 604/95.04 |
| 2006/0100640 A1* | 5/2006 | Bolduc ........... A61B 17/00234 606/108 |
| 2007/0016164 A1* | 1/2007 | Dudney ............ A61M 25/0136 604/523 |
| 2007/0156116 A1 | 7/2007 | Gonzales |
| 2011/0257499 A1* | 10/2011 | de la Rama ........ A61B 5/0422 600/373 |
| 2012/0089125 A1* | 4/2012 | Scheibe ........... A61M 25/0147 604/523 |
| 2012/0197236 A1 | 8/2012 | Randolph |
| 2012/0203170 A1 | 8/2012 | Potter |
| 2012/0209143 A1* | 8/2012 | Schultz ............. A61M 25/0136 600/585 |
| 2013/0018307 A1 | 1/2013 | Lee et al. |
| 2013/0096553 A1 | 4/2013 | Hill et al. |
| 2013/0144209 A1 | 6/2013 | Ryan |
| 2013/0172813 A1 | 7/2013 | Caples et al. |
| 2014/0276222 A1* | 9/2014 | Tegg ................. A61M 25/0136 600/585 |
| 2014/0276645 A1* | 9/2014 | Lam .................. A61M 25/0105 604/528 |

FOREIGN PATENT DOCUMENTS

| | | |
|---|---|---|
| EP | 0452402 | 6/1995 |
| EP | 0790066 | 8/1997 |
| EP | 0868923 | 5/1999 |
| EP | 0980693 | 1/2005 |
| EP | 20022859 | 12/2008 |
| EP | 1832307 | 4/2010 |
| EP | 1803481 | 9/2010 |
| EP | 2438954 | 4/2012 |
| EP | 2583616 | 4/2013 |
| EP | 2609886 | 7/2013 |
| JP | H7-255855 | 9/1995 |
| WO | 1992004933 | 4/1992 |
| WO | 1994012089 | 6/1994 |
| WO | 1999006095 | 2/1999 |
| WO | 2002089891 | 11/2002 |
| WO | 2005113050 | 12/2005 |
| WO | 2006011931 | 2/2006 |
| WO | 2009082570 | 7/2009 |
| WO | 2010035599 | 4/2010 |

OTHER PUBLICATIONS

Japan Patent Office, "Notification of Reasons for Rejection" issued in counterpart Japanese Patent Application No. 2016-545267. Dated: Mar. 7, 2017.

* cited by examiner

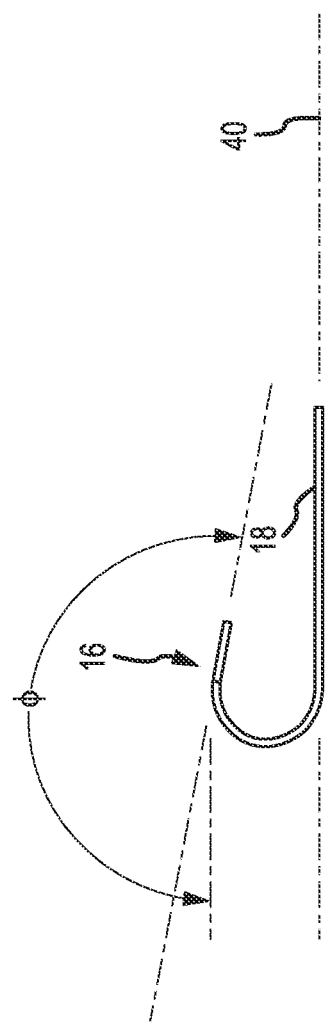
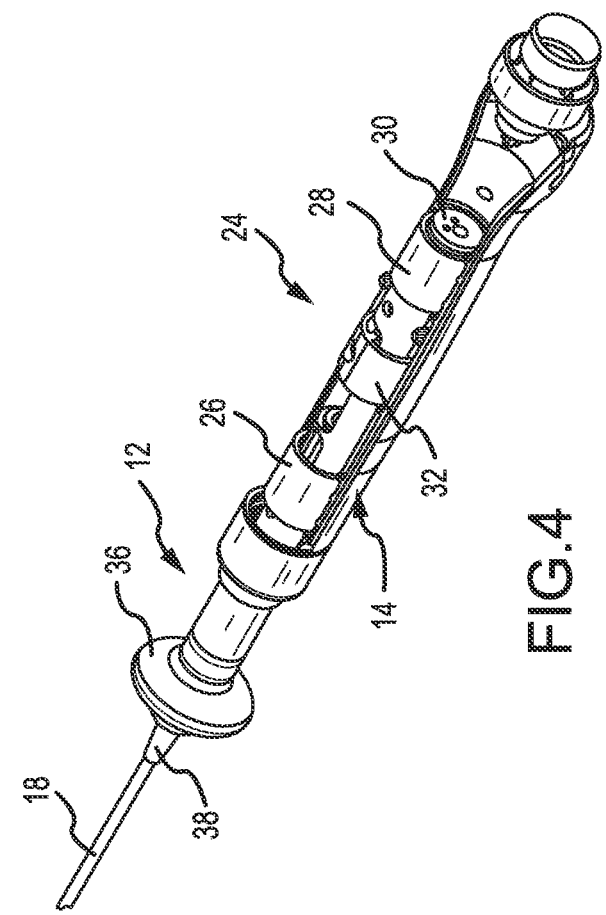

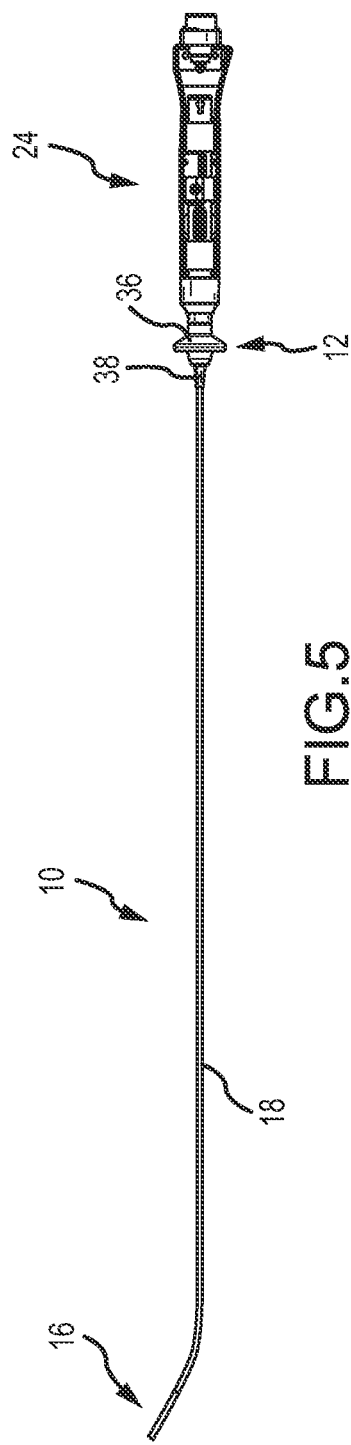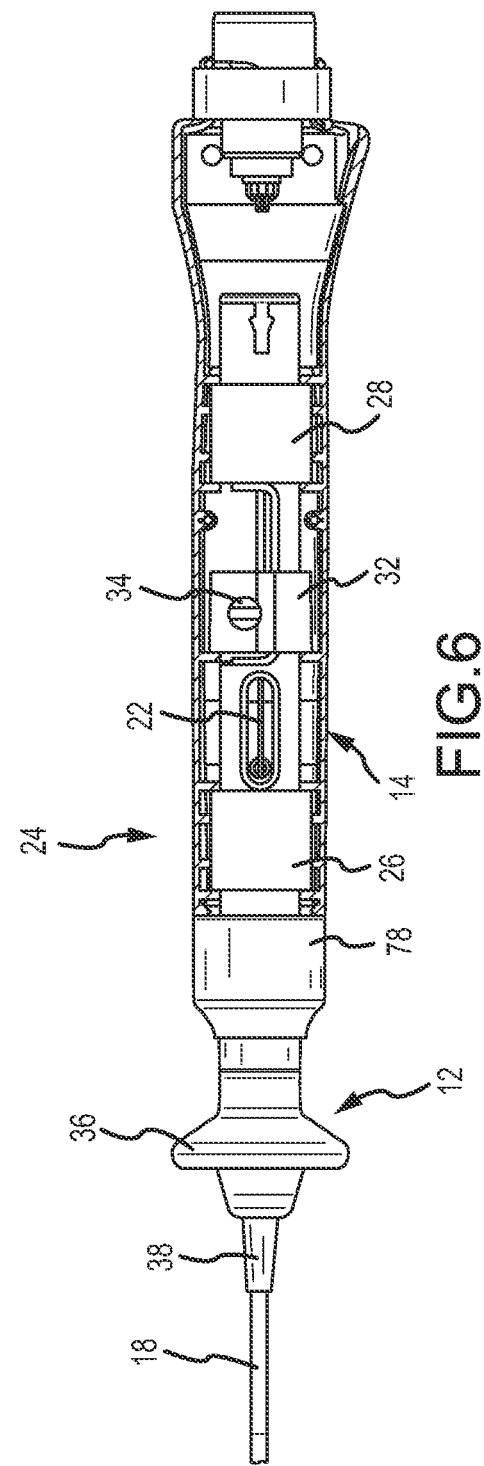
FIG.5
FIG.6

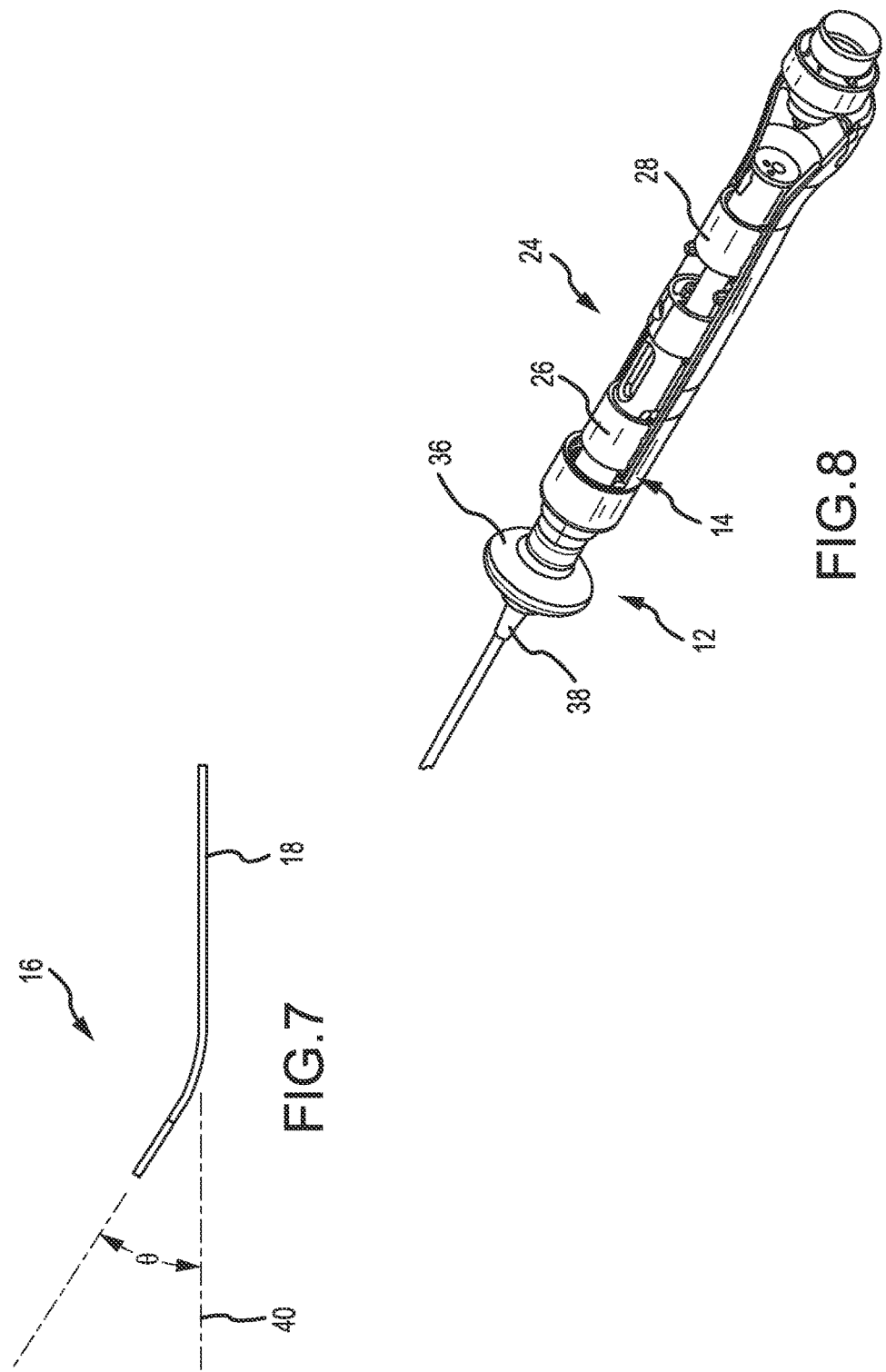

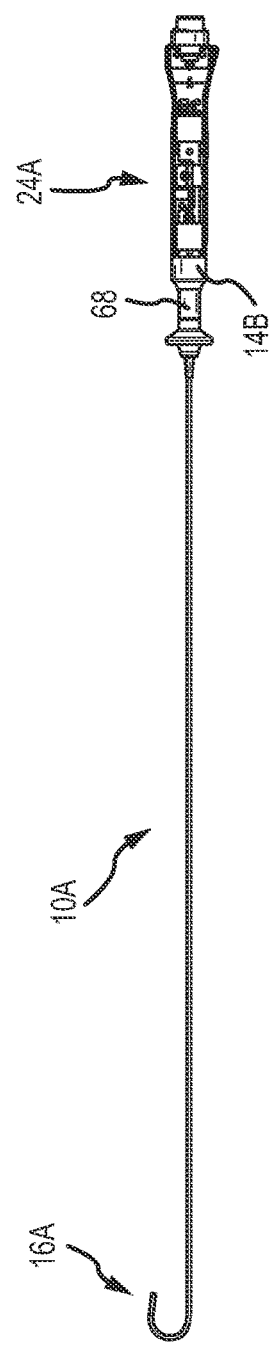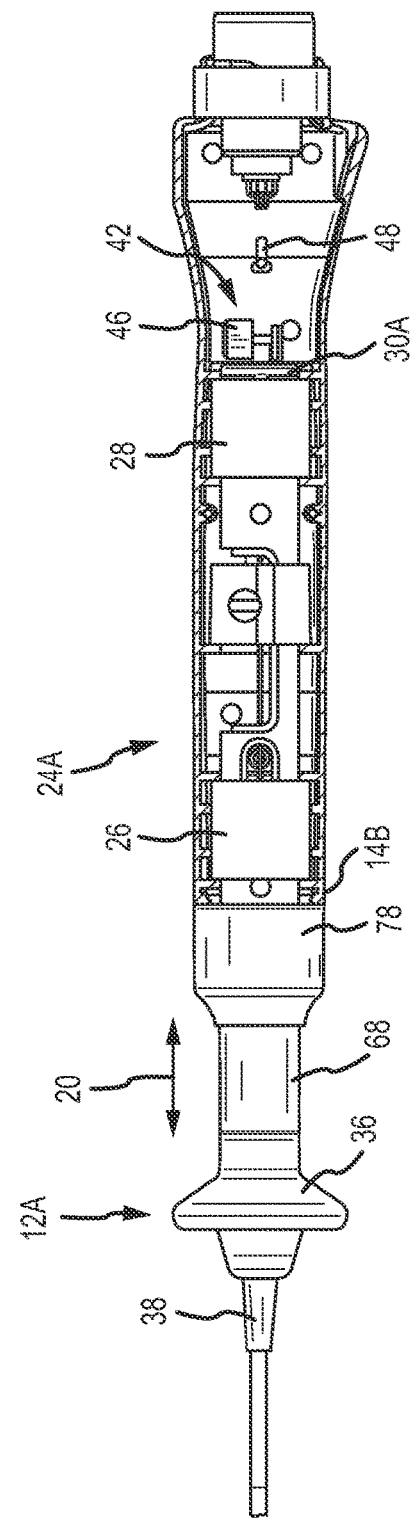

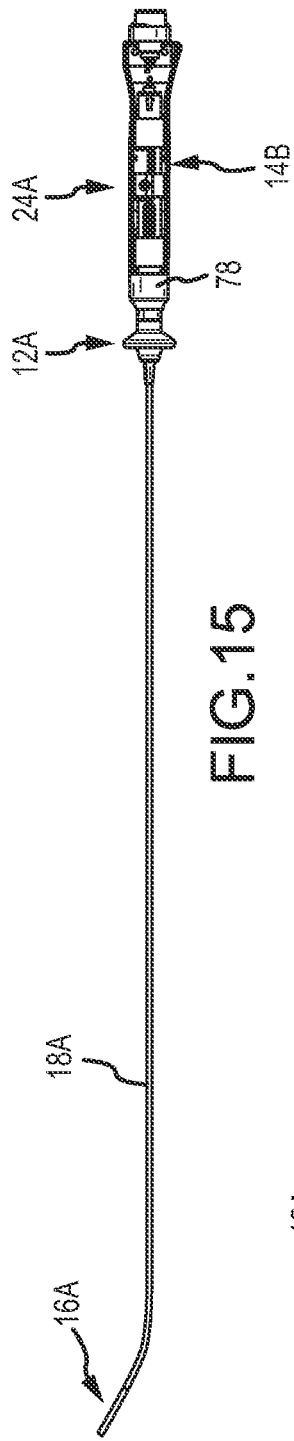
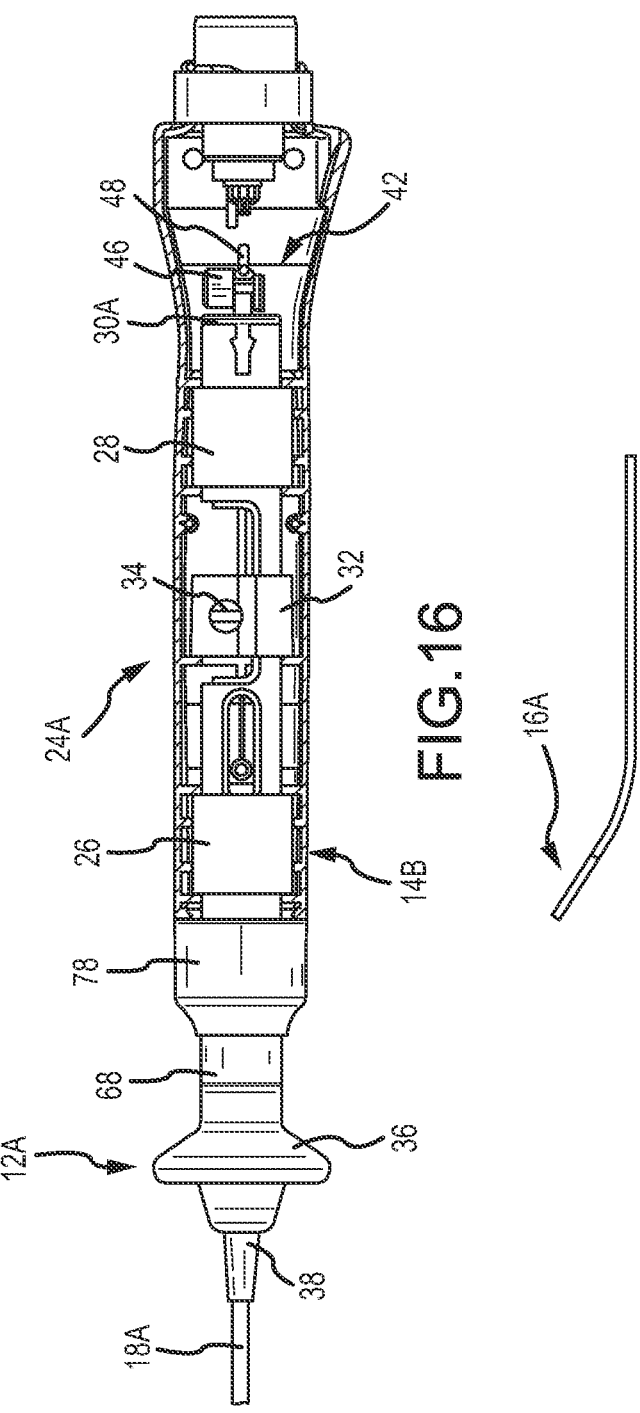
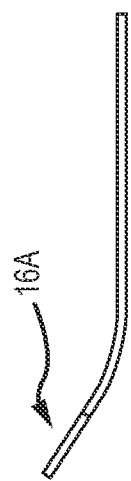
FIG. 15
FIG. 16
FIG. 17

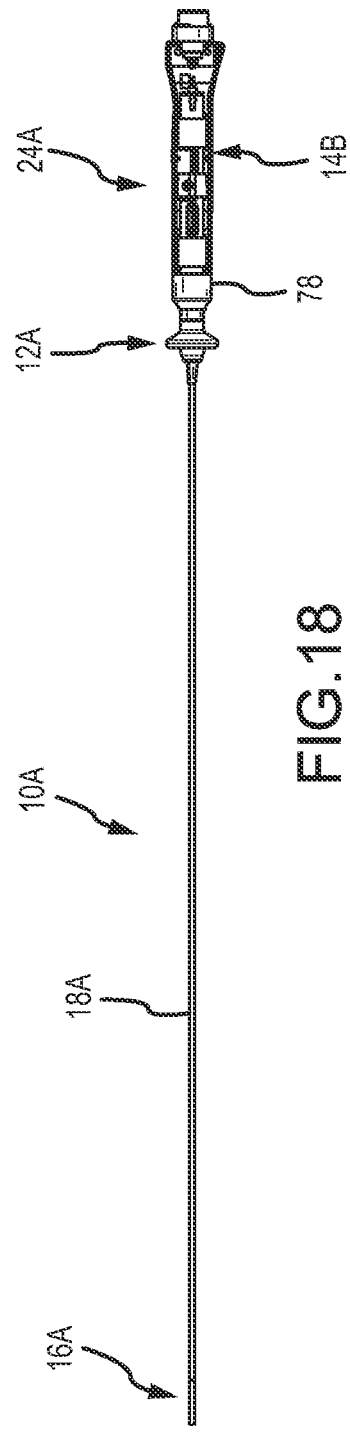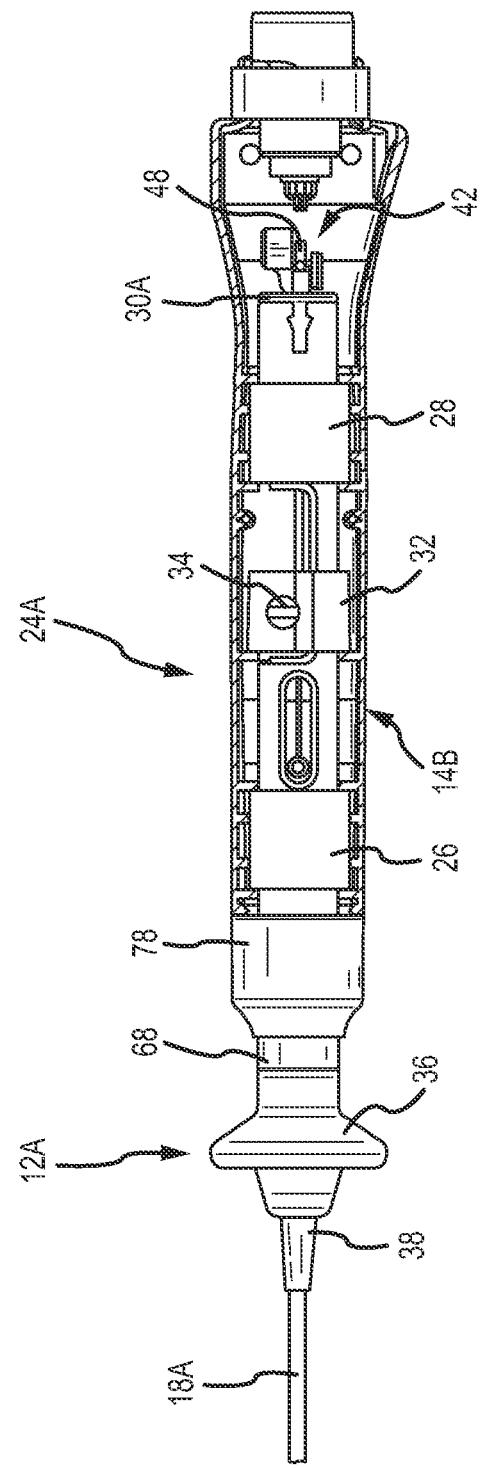

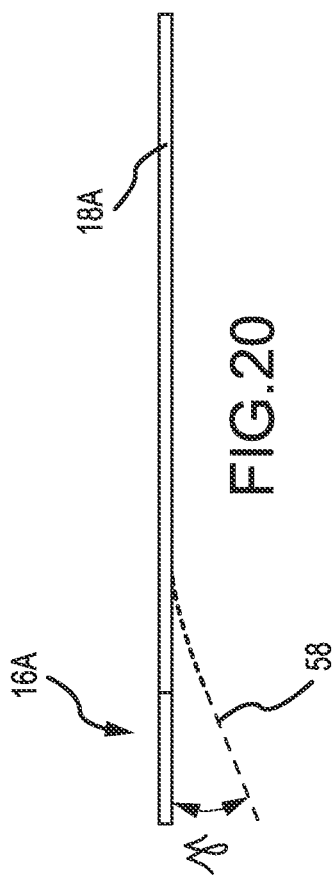
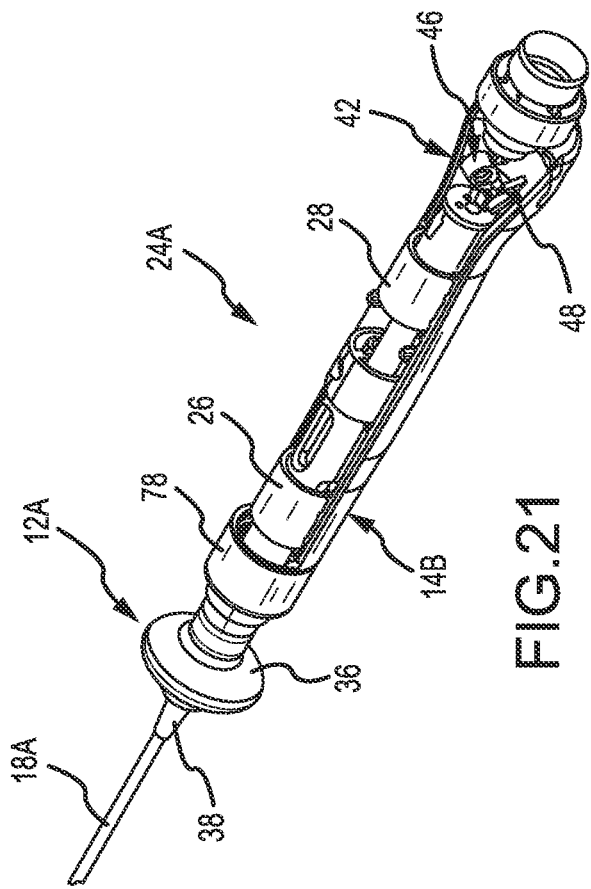

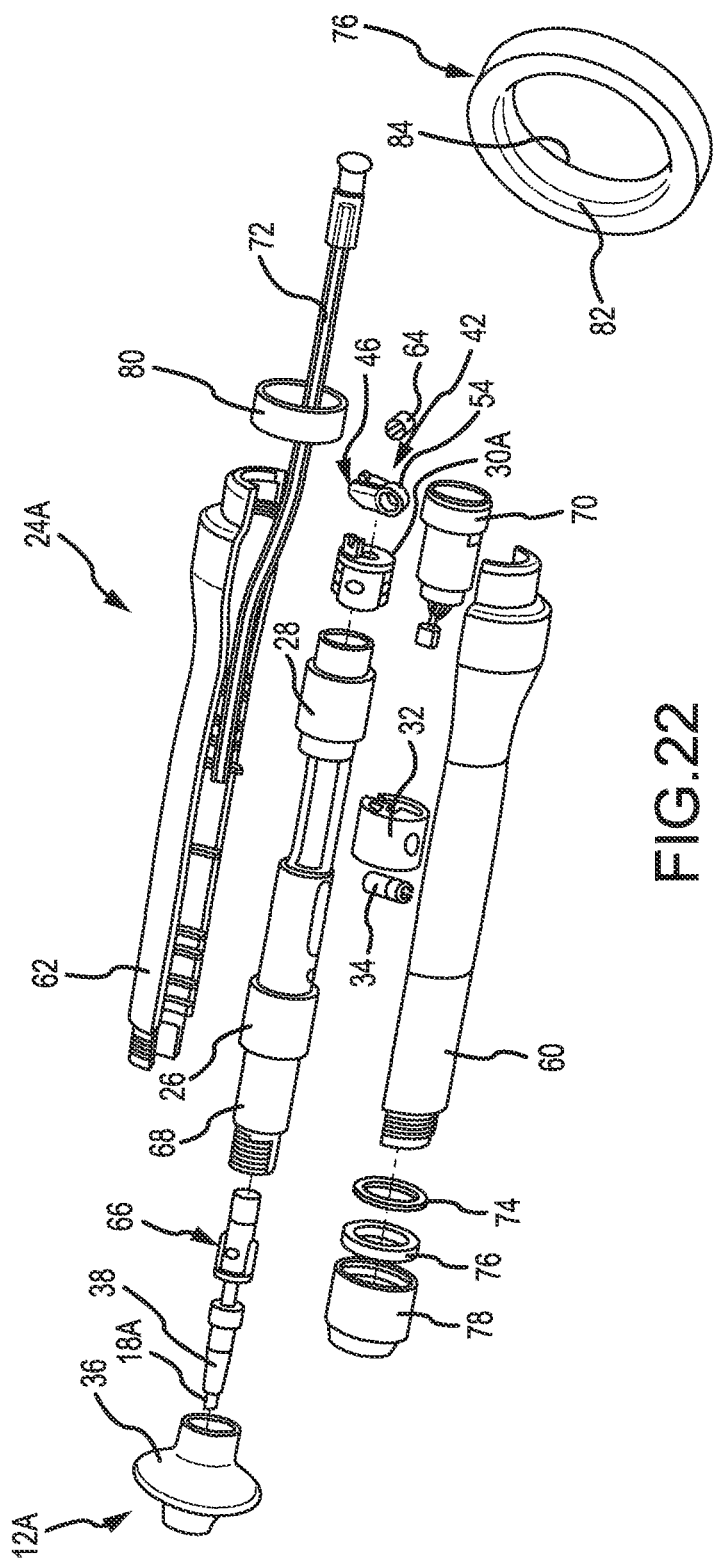

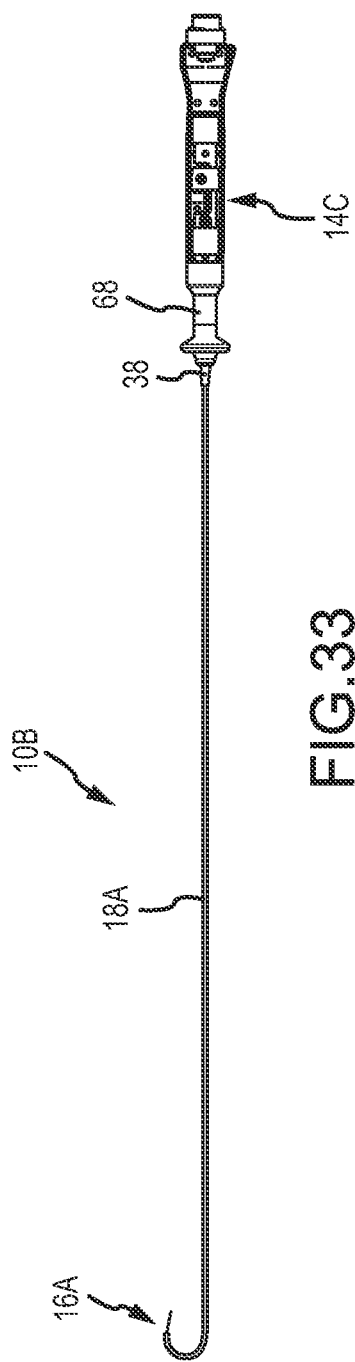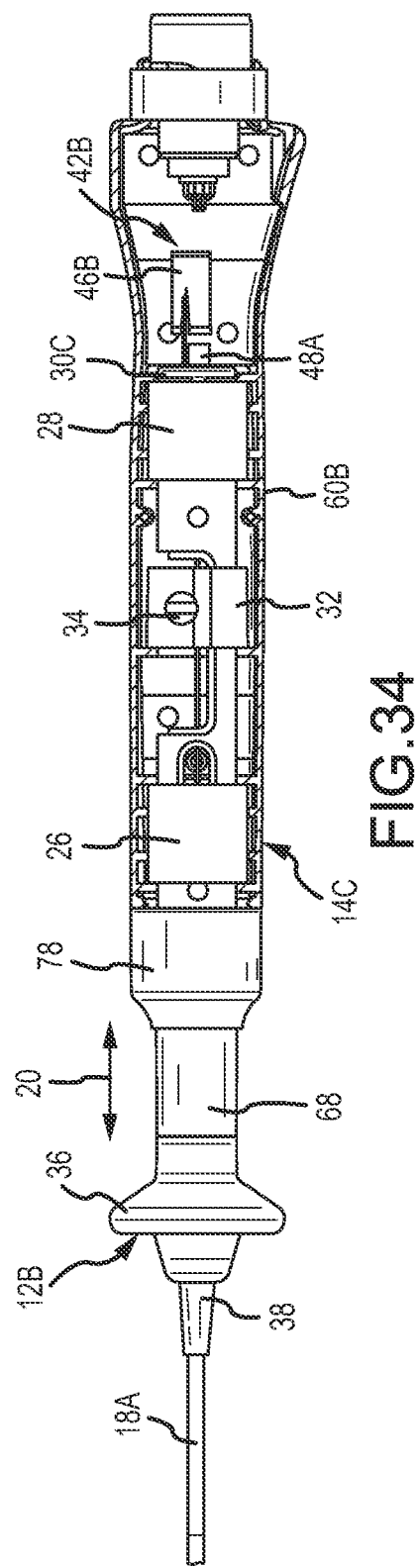

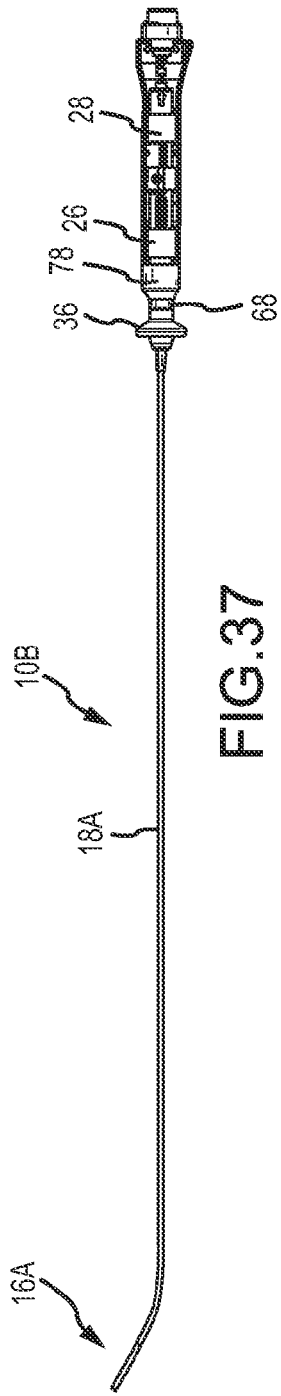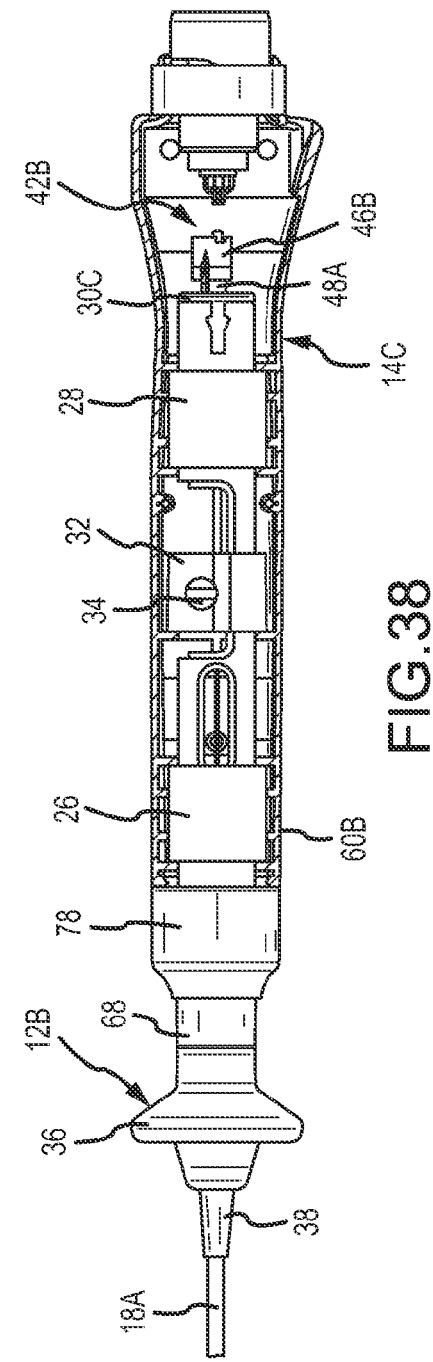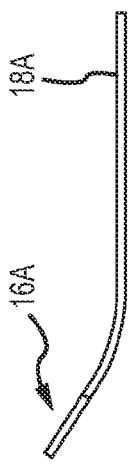
FIG. 37
FIG. 38
FIG. 39

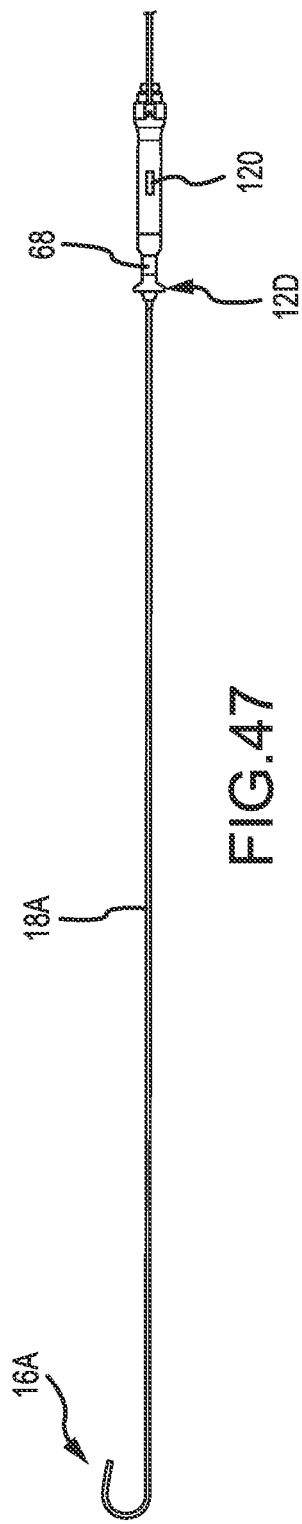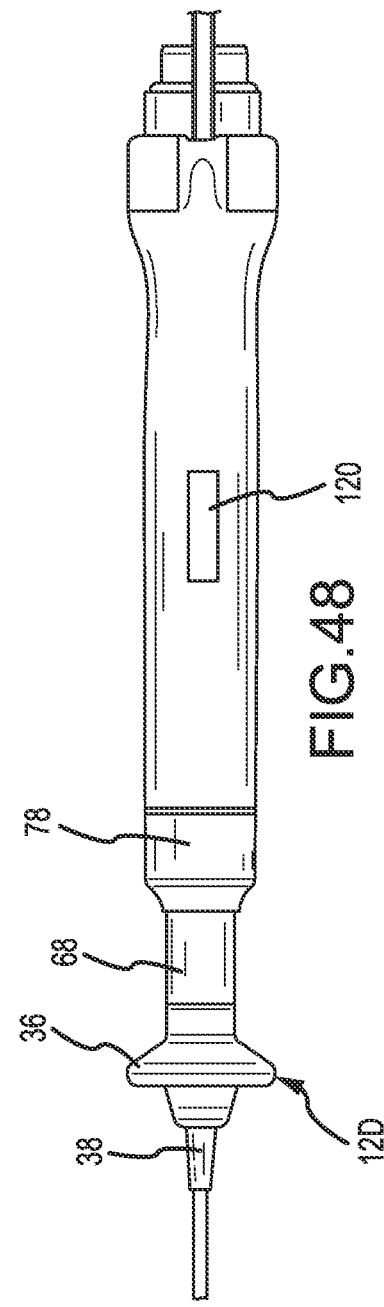

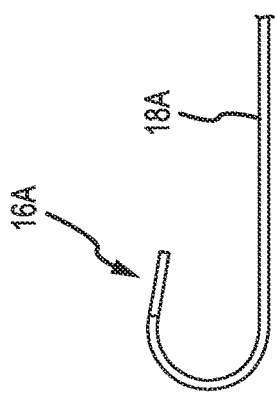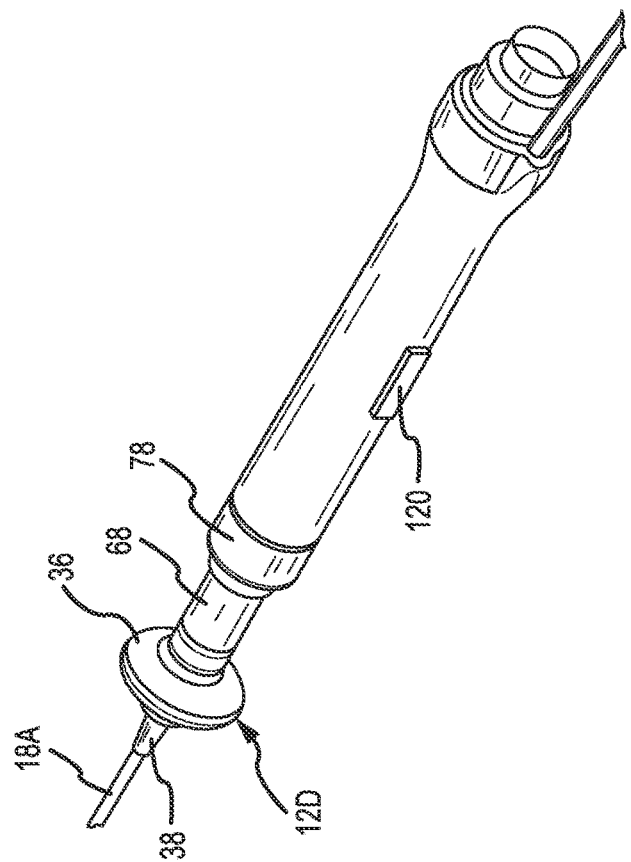

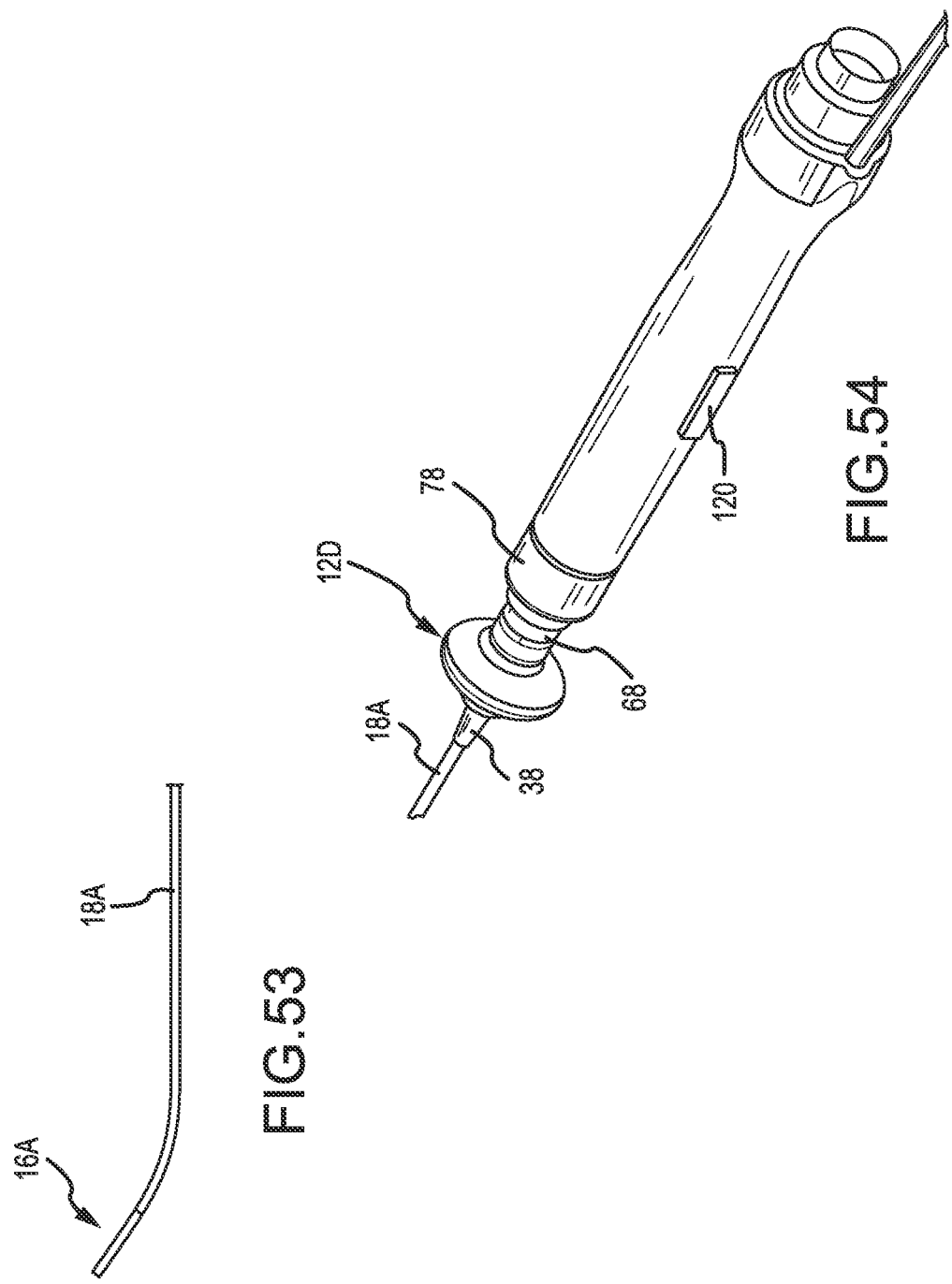

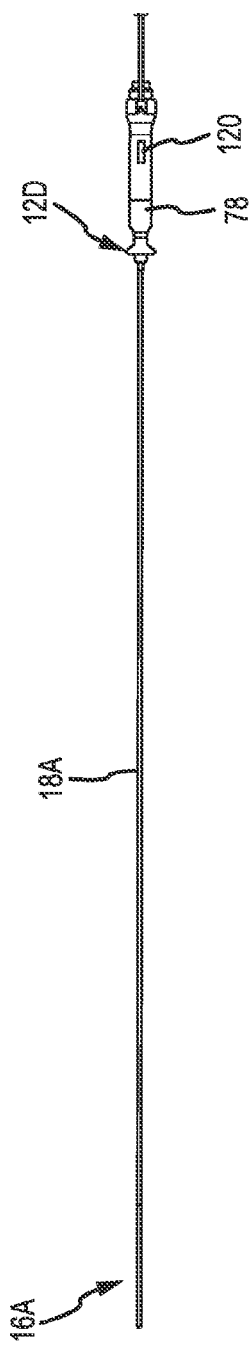
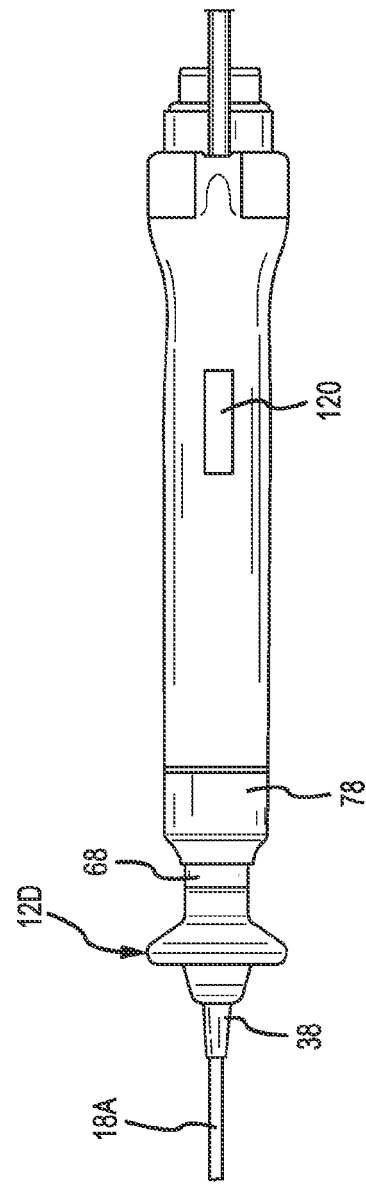

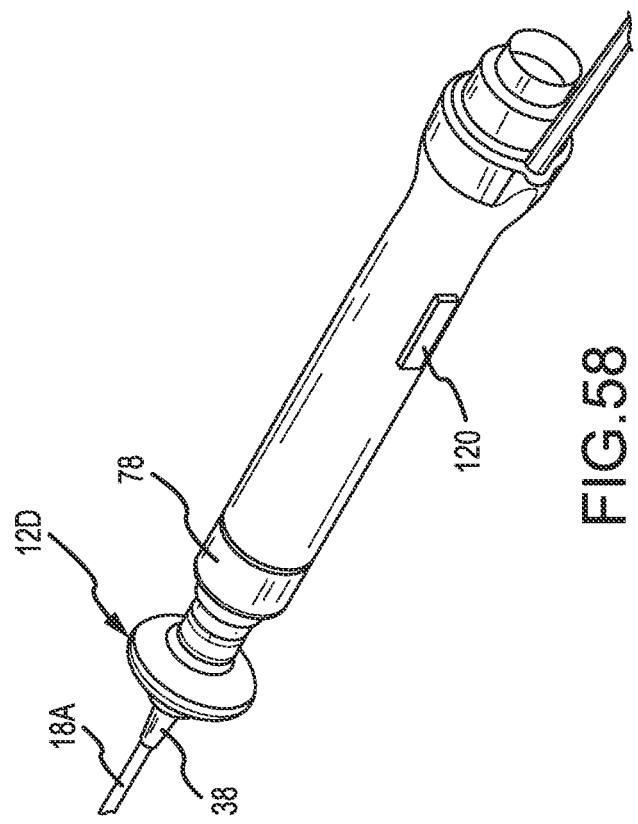
FIG.57
FIG.58

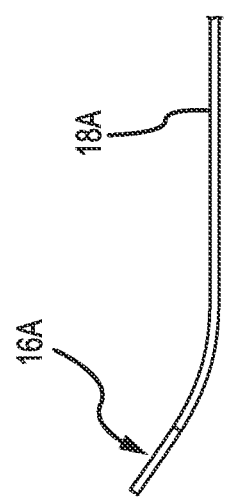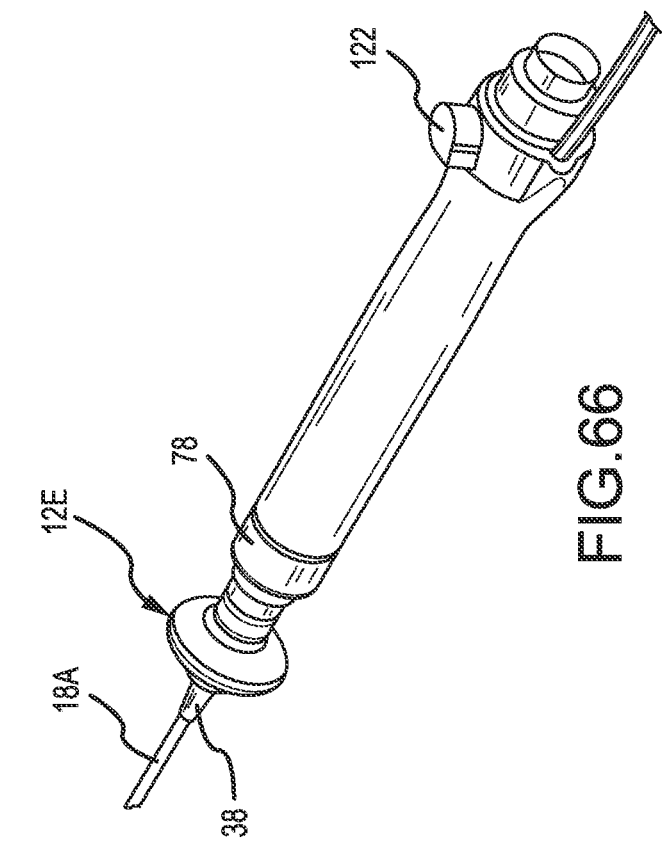

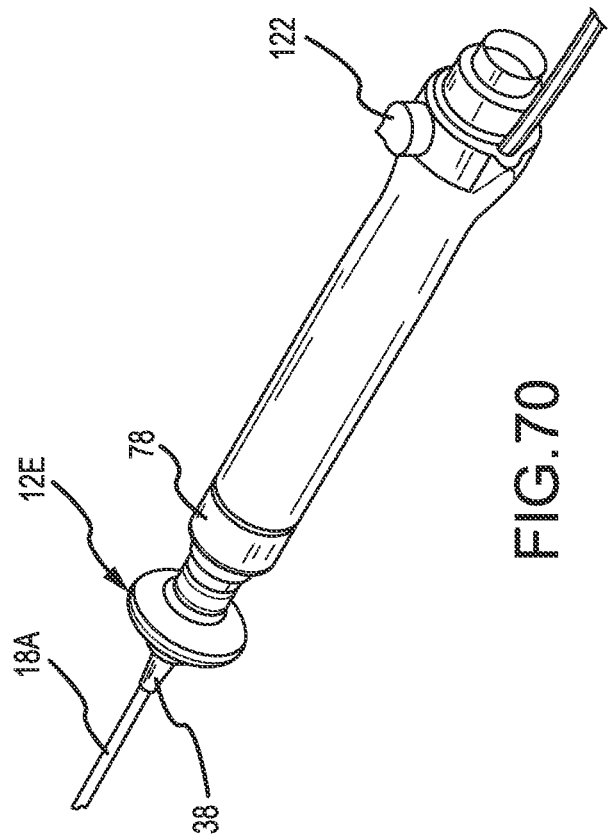

CATHETER HAVING AN ACTIVE RETURN-TO-STRAIGHT MECHANISM

CROSS-REFERENCE TO RELATED APPLICATIONS

This application claims the benefit of U.S. provisional application No. 61/884,897, filed 30 Sep. 2013, which is hereby incorporated by reference as though fully set forth herein.

BACKGROUND a. Field

The instant disclosure relates to actuators for steerable medical devices. In particular, the disclosure relates to actuators comprising active return-to-straight mechanisms employing one or more tension members.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. In some procedures, the catheter imparts ablative energy to cardiac tissue to create one or more lesions in the cardiac tissue. These lesions disrupt undesirable cardiac activation pathways and thereby limit, corral, or otherwise prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a pull wire or other tension member attached or anchored at the distal end of the catheter and extending proximally to an actuator in a control handle that controls the application of tension on the pull wire.

The foregoing discussion is intended only to illustrate the present field and should not be taken as a disavowal of claim scope.

BRIEF SUMMARY

It is desirable to be able to ensure that a deflectable portion of a catheter shaft may be returned to a substantially straight configuration whenever desired throughout a medical procedure, even if the catheter becomes less responsive as the medical procedure progresses. It is also desirable to be able to tailor total deflectability of the catheter distal portion and, independent of the targeted total deflectability, maintain the ability to return the deflectable distal portion of the catheter shaft to a substantially straight configuration whenever desired.

In one embodiment, an apparatus comprises a deflection actuator configured to cause deflection of a distal portion of a catheter from an initial position; a first return actuator configured to partially reverse the deflection of the distal portion of the catheter; and a second return actuator configured to continue reversing the deflection of the distal portion of the catheter towards the initial position.

In another embodiment, a deflectable catheter comprises a catheter shaft, a deflection actuator, and a handle housing that at least partially houses the deflection actuator. The catheter shaft comprises a shaft proximal end, a shaft distal end, a shaft deflectable distal portion, and first and second tension members extending from the shaft proximal end to the shaft deflectable distal portion. The deflection actuator, which is operatively coupled to the first and second tension members, comprises an active return-to-straight mechanism, which itself comprises (i) a primary or gross return actuator and (ii) a secondary or fine return actuator.

The foregoing and other aspects, features, details, utilities, and advantages of the present invention will be apparent by reading the following description and claims, and from reviewing the accompanying drawings.

BRIEF DESCRIPTION OF THE DRAWINGS

FIG. 3 is an enlarged, fragmentary view of the distal tip section of the catheter depicted in FIG. 1, showing the catheter tip portion in a fully-deflected configuration.

FIG. 4 is a fragmentary, isometric view similar to FIG. 2.

FIG. 5 depicts the catheter also shown in FIGS. 1-4, but in a neutral position with the plunger fully retracted into the handle.

FIG. 6 is similar to FIG. 2, but depicts the plunger fully retracted into the handle.

FIG. 7 is similar to FIG. 3, but shows how the catheter tip may not return to a straight configuration despite the plunger having returned to a neutral (i.e., fully-retracted) position.

FIG. 8 is a fragmentary, isometric view similar to FIG. 4, but showing the plunger in a fully-retracted configuration.

FIG. 11 is similar to FIG. 1, again depicting a plunger-type catheter in a fully-actuated configuration, but in FIG. 11 an active return-to-straight mechanism is visible near the proximal end of the handle.

FIG. 12 is an enlarged, fragmentary view of the handle depicted in FIG. 11, with the upper handle housing removed to show the active return-to-straight mechanism while the catheter tip is in its fully-deflected configuration.

FIG. 15 is most similar to FIG. 5, but depicts the catheter also shown in FIGS. 11-14 in a semi-neutral portion, wherein the plunger is partially retracted into the handle housing.

FIG. 16 is an enlarged, fragmentary view of the handle depicted in FIG. 15.

FIG. 17 is an enlarged, fragmentary view of the catheter tip portion in its at-rest position also shown in FIG. 15.

FIG. 18 depicts the catheter shown in FIGS. 11-17 with the handle in its fully-retracted configuration and its distal tip portion in its neutral configuration (i.e., straight or substantially straight configuration).

FIG. 19 is an enlarged, fragmentary view of the handle depicted in FIG. 18, with the upper handle housing removed and more clearly showing the active return-to-straight mechanism in its actuated position.

FIG. 20 is an enlarged, fragmentary view of the distal deflectable portion of the catheter shaft depicted in FIG. 18, showing the tip portion of the catheter in its substantially straight configuration and showing, in phantom, that the active return-to-straight mechanism may be pre-set so as to deflect the distal portion of the catheter slightly in the opposite direction when the plunger is fully retracted into the handle housing.

FIG. 21 is a fragmentary, isometric view of the catheter handle in the configuration also shown in FIG. 19.

FIG. 22 is an exploded, isometric view of the components comprising the catheter actuator also shown in FIGS. 11-21.

FIG. 23 is an enlarged, isometric view of the compression ring also shown in FIG. 22.

FIGS. 33-36 are similar to FIGS. 11-14, respectively, but depict an alternative configuration of the return-to-straight mechanism, wherein an alternative lever is pivotably mounted to the lower handle housing.

FIGS. 37-39 are similar to FIGS. 15-17, respectively, but depict the actuator shown to good advantage in FIGS. 34 and 36 when the plunger is in a semi-neutral configuration (i.e., when the plunger is partially retraced into the handle housing), before the return-to-straight mechanism also shown in, for example, FIGS. 34 and 36 has been actuated.

FIGS. 47-50 are comparable to, for example, FIGS. 33-36, respectively, but depict an active return-to-straight mechanism comprising a second, manual actuator when the catheter shaft is in a fully-deflected configuration (e.g., when the plunger is fully extended from the handle housing).

FIGS. 51-54 are similar to FIGS. 47-50, respectively, but depict the plunger fully retracted into the handle housing, before the second, manual actuator is actuated.

FIGS. 55-58 are similar to FIGS. 51-54, respectively, but FIGS. 55, 56, and 58 show the second, manual actuator in its fully-actuated configuration, which returns the distal tip portion (or section) of the catheter to its substantially straight configuration shown in FIGS. 55 and 57.

FIGS. 63-66 are most similar to FIGS. 51-54, respectively, with the plunger fully retracted into the handle housing, before the second, manual actuator is actuated.

FIGS. 67-70 are most similar to FIGS. 55-58, respectively, with the plunger fully retracted into the handle housing, but with the second, manual actuator actuated, which places the distal deflectable section of the catheter shaft in its substantially straight configuration shown in FIGS. 67 and 69.

DETAILED DESCRIPTION OF EMBODIMENTS OF THE INVENTION

Referring first to FIGS. 1-10, an embodiment of a unidirectional, plunger-type catheter 10 that does not have an active return-to-straight mechanism is described first. While various embodiments are described herein in the context of a uni-directional catheter, it should be recognized that the disclosed principles are equally applicable to catheters capable of deflecting in more than one direction, where at least one of the deflections is not configured to deflect in a direction opposite the deflection and beyond its "undeflected" or neutral position. For example, the principles described herein are also applicable to a catheter configured to deflect from a substantially straight configuration (as used herein, the terms "substantially straight" and "straight," as in "return-to-straight," describe a configuration of the catheter shaft wherein the distal tip portion of the catheter shaft is aligned with, or substantially aligned with, the portion of the catheter shaft immediately proximal of the distal tip portion) to a first arc in a first plane, and also to deflect from the substantially straight configuration to a second arc in a second plane (e.g., 90 degrees apart from the first plane), whereby one or both of the deflections are configured such that they do not deflect in opposite directions in their respective planes significantly beyond the substantially-straight orientation. As another example, the principles described herein are also applicable to a catheter shaft exhibiting some distal deflection in its "neutral position," and is configured to deflect the distal portion toward, away from, or otherwise relative to this pre-deflected neutral position when actuated, and to complete a return actuation substantially to the initially deflected neutral position. It should also be noted that the principles disclosed herein are equally applicable to deflection mechanisms other than plunger-type mechanisms, although various embodiments herein are described in the context of an axially-actuated, plunger-type catheter.

Figure 1:
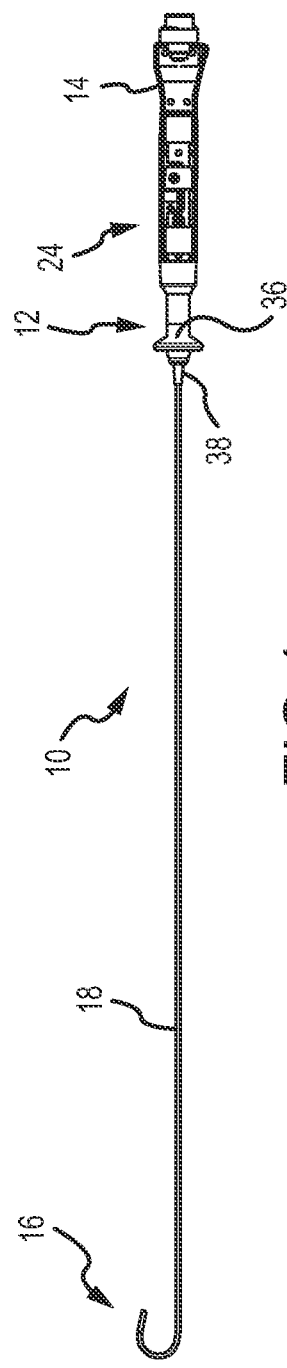
FIG. 1 depicts a plunger-type catheter without an active return-to-straight mechanism, shown with the upper handle housing removed and with a tip portion in a fully-deflected configuration.

FIG. 1 depicts the entire catheter 10 in a fully-actuated configuration, with the plunger assembly 12 fully advanced from (i.e., pushed distally and fully extended from) the handle housing 14, which fully deflects the distal tip section 16 of the catheter shaft 18, as shown to good advantage in FIGS. 1 and 3. The plunger assembly 12 can be moved proximally and distally into and out of, respectively, the handle housing 14 as represented by the double-headed arrow 20 in FIG. 2. In this configuration, an active deflection element 22 (e.g., an active tension member or pull wire or puller wire or tension strand or tension cord or tension fiber) has been fully actuated, thereby fully deflecting the catheter tip section 16. In FIG. 1, and in FIGS. 2 and 4, the upper handle housing has been removed to reveal certain features inside of the handle or actuator 24.

Figure 2:
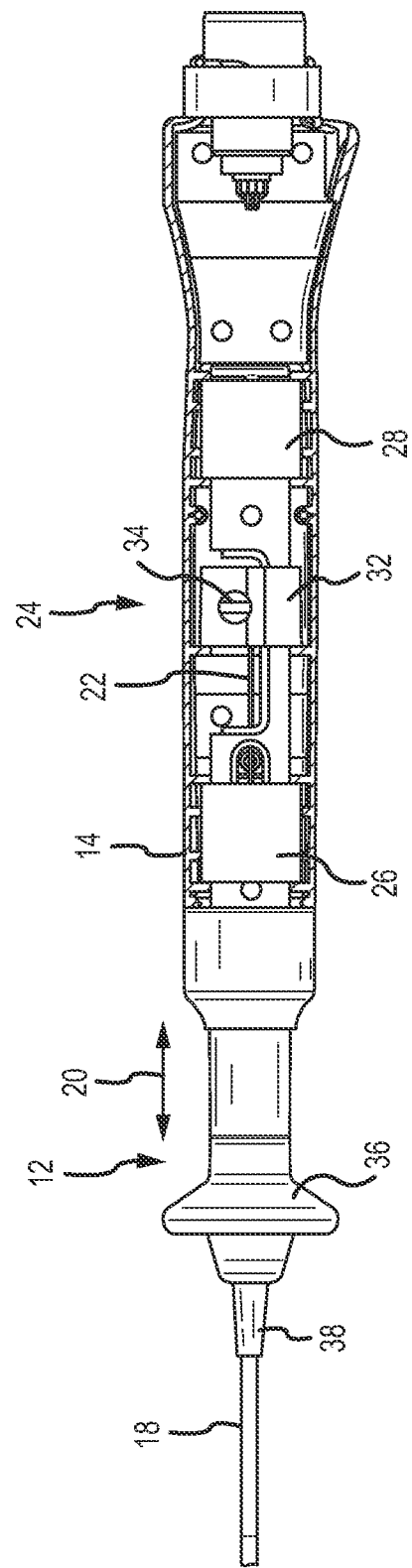
FIG. 2 is an enlarged, fragmentary view of the handle also depicted in FIG. 1, again shown with the upper handle housing removed to show the inner workings of the catheter actuator.

As shown in good advantage in FIGS. 2 and 4, with the plunger assembly 12 pushed distally as shown, the plunger assembly 12 is in its most distal position relative to the sleeve bearings 26, 28 slidably supporting the plunger assembly in the handle housing 14. A plunger cap 30 comprising the proximal part of the plunger assembly 12 may be clearly seen in FIG. 4. A gripper 32 comprising a wire anchor 34 is also visible in both FIGS. 2 and 4. At the distal end of the plunger assembly 12 is a thumb boss or thumb gripper 36. During use of the catheter, the user, most likely an electrophysiologist or other physician, will generally grip the handle housing with the fingers of one hand and push or pull on the thumb boss 36 with the thumb of the gripping hand. As also shown in FIGS. 2 and 4, distal from the thumb boss is a strain relief 38, which supports the proximal portion of the catheter shaft 18. As shown to good advantage in FIG. 3, in this configuration, the distal section 16 of the catheter shaft 18 is fully deflected relative to the shaft longitudinal axis 40. In particular, the angle phi (Φ) in FIG. 3 represents the maximum deflection angle of the distal section 16 of the catheter shaft 18. In this particular view, the maximum deflection angle phi is approximately 190 degrees. For purposes of the present invention, however, the maximum deflection angle may vary widely.

Referring next most particularly to FIGS. 5-8, further aspects of the catheter 10 that does not include an active return-to-straight mechanism will be described. In the configuration shown in FIGS. 5-8, the plunger assembly 12 has been fully retracted into the handle housing 14 as shown to best advantage in FIGS. 6 and 8 (compare, for example, FIG. 2 to FIG. 6, or FIG. 4 to FIG. 8). However, as shown in FIGS. 5 and 7, even though the plunger assembly 12 has been pulled fully into the handle housing 14 to its maximum extent, the distal section 16 of the catheter shaft 18 remains partially deflected relative to the catheter longitudinal axis 40 by an angle theta (θ) labeled in FIG. 7.

Figure 9:
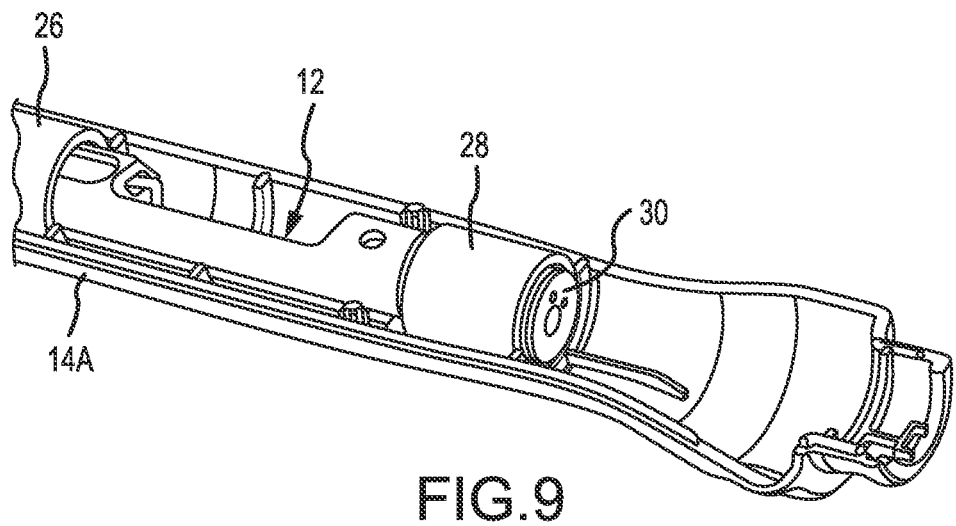
FIG. 9 is a fragmentary, isometric view of a plunger-type mechanism in a lower handle housing with the plunger mechanism in a fully-actuated position.
Figure 10:
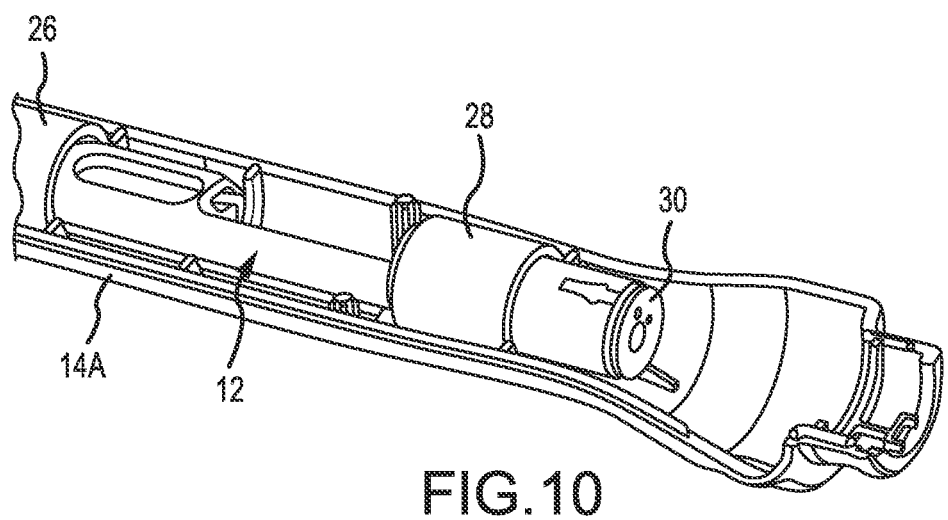
FIG. 10 is a fragmentary, isometric view similar to FIG. 9, but shows the plunger in a fully-retracted or neutral position.

FIG. 9 is a fragmentary, isometric view of a plunger-type mechanism 12 in a handle housing 14A with the plunger assembly 12 in a fully-actuated position, similar to what is shown in FIGS. 1-4. In FIG. 9, however, the handle housing 14A has a configuration that is slightly different from the handle housing 14 configuration shown in, for example, FIGS. 2 and 4. FIG. 10 is a fragmentary, isometric view similar to FIG. 9, but shows the plunger assembly 12 in a fully-retracted or neutral position.

In circumstances where it is highly desirable or preferable to be able to get the distal tip section 16 of the catheter shaft 18 to return to a substantially-straight configuration rather than merely to the slightly bent configuration depicted in FIGS. 5 and 7, an active return-to-straight mechanism, such as those described below, may be utilized.

Figure 14:
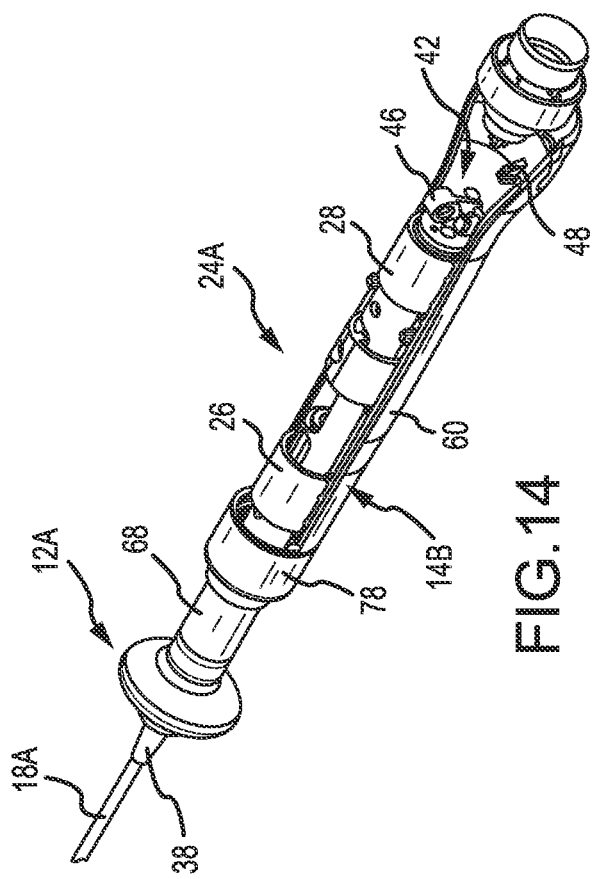
FIG. 14 is a fragmentary, isometric view of the catheter in the fully-deflected configuration also shown in FIG. 12.
Figure 13:
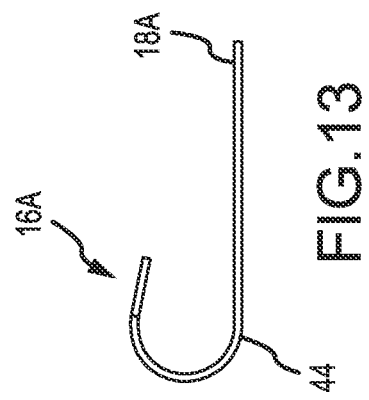
FIG. 13 is similar to FIG. 3 and depicts the distal section of the catheter in a fully-deflected configuration.

FIGS. 11-29 depict a uni-directional catheter 10A having an active return-to-straight mechanism 42 according to a first embodiment. In FIGS. 11-14, the uni-directional catheter 10A is depicted in its fully-actuated configuration, with its distal tip section (or shaft deflectable distal section) 16A in its fully-deflected configuration. The shaft deflectable distal portion starts from a deflection commencement point 44 (see, e.g., FIG. 13) located at a proximal end of the shaft deflectable distal portion 16A. FIG. 11 depicts the entire catheter 10A in this fully-actuated configuration, with the upper handle housing removed to reveal details within the handle 24A. FIG. 12 is an enlarged view of the handle 24A depicted in FIG. 11. In this view, the plunger assembly 12A has been fully advanced distally. In this figure, a first embodiment of a lever 46 comprising part of the active return-to-straight mechanism 42 is depicted in an unactuated configuration and separated by a space from an actuation boss 48 which, in this embodiment, comprises part of (or is mounted onto) a handle housing 14B. FIG. 13 is an enlarged, fragmentary view of the distal tip section 16A of the catheter shown in its fully-deflected configuration. FIG. 13 is similar to FIG. 3. FIG. 14 is an isometric, fragmentary view of the actuator 24A as also shown in FIGS. 11 and 12, and again clearly shows that the lever 46 of the return-to-straight mechanism 42 has not been actuated.

FIGS. 15-17 are most similar and correspond to FIGS. 11-13, respectively. In FIGS. 15-17, however, the plunger assembly 12A has been partially retracted into the handle housing 14B. This may be clearly seen by comparing FIG. 16 to FIG. 12 and noting the distance between the thumb boss 36 and the distal end of the handle housing 14B. In particular, in FIG. 16, the thumb boss 36 is closer to the handle housing 14B then it is in FIG. 12. When the plunger assembly 12A is in the configuration shown to best advantage in FIG. 16, the return-to-straight mechanism 42 has not yet been actuated. For instance, the lever 46 that is pivotably mounted to the proximal end of the plunger assembly 12A has not yet been pivoted away from the plunger cap 30A. With the catheter 10A in this configuration, the distal tip section 16A of the catheter has returned toward straight from the configuration depicted in, for example, FIGS. 11 and 13, but the catheter tip section 16A remains partially deflected as shown in FIGS. 15 and 17.

Referring next to FIGS. 18-21, activation of an embodiment of the active return-to-straight mechanism 42 will be described. FIG. 18 depicts the entire catheter 10A in a neutral position, where the plunger assembly 12A is fully retracted into the handle housing 14B and the catheter shaft 18A is substantially straight. FIG. 19 is an enlarged, fragmentary view of the handle 24A as shown in FIG. 18. Again, the plunger assembly 12A is fully retracted into the handle housing in this configuration. This may be clearly seen by comparing, for example, FIG. 19 to FIGS. 12 and 16. In particular, in FIG. 19, the thumb boss 36 is closer to the handle housing 14B then it is in FIGS. 12 and 16.

As shown to good advantage in FIGS. 19 and 21, when the plunger assembly 12A is fully retracted, the active return-to-straight mechanism 42 has been actuated. In particular, the actuation boss 48 mounted on (or comprising an integral part of) the housing 14B has engaged the actuation pin or segment 50 (see, for example, FIG. 29) comprising part of the lever, thereby pivoting the lever 46 about the pivot pin 52 and moving the tuner drum 54 (see FIG. 29) away from the plunger cap 30A and pulling the inactive deflection element 56 (see FIG. 26) proximally to thereby fully straighten the distal tip section 16A of the catheter shaft 18A to the substantially straight configuration shown in FIGS. 18 and 20.

In some embodiments, the return mechanism may be configured to return the catheter shaft to a substantially straight position when the user actuation mechanism (e.g., the plunger assembly) has been returned to its neutral position, while in other embodiments, the return mechanism may be configured to return the catheter shaft to somewhat less than straight or somewhat more than straight (i.e., such that the deflectable section 16A deflects slightly beyond the longitudinal axis of the catheter shaft). This latter possibility is represented, for example, by the dash line 58 and the angle gamma ($\gamma$) in FIG. 20.

By designing the return-to-straight mechanism to be able to deflect the catheter shaft in the opposite direction, as shown by the dash line 58 in FIG. 20, it may be impossible to return the catheter shaft to a substantially straight configuration during an entire medical procedure. In particular, as the catheter is used during a procedure, its performance may degrade as the catheter shaft takes on fluid, or as the pull wires stretch, or as the deflection mechanism wares. Thus, it may be desirable to design the uni-directional catheter so that it may, at least at commencement of use, return the deflectable section 16A past straight by the small angle gamma ($\gamma$) shown in FIG. 20 to ensure that a physician is able to return the catheter shaft 18A to a substantially straight configuration throughout the procedure. That is, the active return-to-straight mechanism may be designed to 'over perform' slightly at the commencement of a procedure. As may be clearly understood from looking at, FIGS. 11-21, this active return-to-straight mechanism is automatically trigged or actuated as the plunger assembly 12A is retracted into the handle housing 14B. That is, the physician need only return the plunger assembly (or gross return actuator or primary actuator) to its neutral position (e.g., fully retract the plunger assembly 12A into the handle housing 14B) to thereby activate the active return-to-straight mechanism 42 (or fine return actuator or secondary actuator), which pulls the distal deflectable section 16A of the catheter shaft to the substantially straight configuration shown in, for example, FIGS. 18 and 20.

FIG. 22 is an exploded, isometric view of a catheter handle 24A having the active return-to-straight mechanism 42 according to the first embodiment and also shown to good advantage in FIGS. 12, 14, 16, 19, and 21. As shown in FIG. 22, the actuator includes a lower handle housing 60 and an upper handle housing 62 having a number of components sandwiched between them. As shown in the central portion of this figure, a plunger assembly is slidably mounted in two sleeve bearings 26, 28. At a proximal end of the plunger, a plunger cap 30A is present. The lever 46 comprising part of the active return-to-straight mechanism 42 is pivotably mounted to the proximal side of the plunger cap 30A. A lever tuner 64 is shown in FIG. 22. In the assembled mechanism, this tuner is threaded into the tuner drum 54 (see FIG. 29) of the lever to attach the otherwise inactive deflection element 56 to the lever 46.

As also shown in FIG. 22, at the distal end of the plunger 12A, a shaft lug 66 and a strain relief 38 are present, and the thumb boss 36 threads onto the plunger body 68. The previously-noted gripper 32 and wire anchor 34 are shown in this figure on the mid-section of the plunger assembly 12A. At the proximal end of the handle housing, a connector 70 is present. As is also shown to good advantage in FIG. 22, a fluid lumen 72 may be present for irrigated configurations. The lower and upper handle housings 60, 62 are held together by a slip washer 74, a compression ring 76, and a handle cap 78 that threads onto the distal ends of the handle housings, and by an assembly ring 80 at the proximal end of the handle housings.

FIG. 23 depicts an enlarged version of one embodiment of the compression ring 76 (also shown in FIG. 22), and more clearly shows a beveled or chamfered inner leading edge 82 of this compression ring. This beveled, inner leading edge helps facilitate smooth movement of the plunger assembly 12A as it is retracted into the handle housing 14B (here comprising the lower handle housing 60 and the upper handle housing 62). More particularly, the chamfered compression ring 76 may serve as a directionally dependent frictional force, such that movement of the plunger 12A in one direction has a lesser frictional force than movement of the plunger in an opposite direction. For example, where the beveled inner leading edge 82 of the compression ring faces distally, plunger actuation in the distal direction (e.g., when deflecting the distal shaft) experiences less friction than when the plunger is actuated in the proximal direction (e.g., when returning the deflection to its neutral position). The chamfered edge of the compression ring can distort into an airspace, due to the beveled edge, when the plunger is moved distally. The non-chamfered edge 84 of the compression ring 76 abuts one or more constraining layers when the plunger is moved proximally, which results in an increased deflection return force relative to the deflection actuation force. This may, for example, facilitate ease of deflection forces while maintaining a deflection "locking" mechanism through a higher return force.

Figure 24:
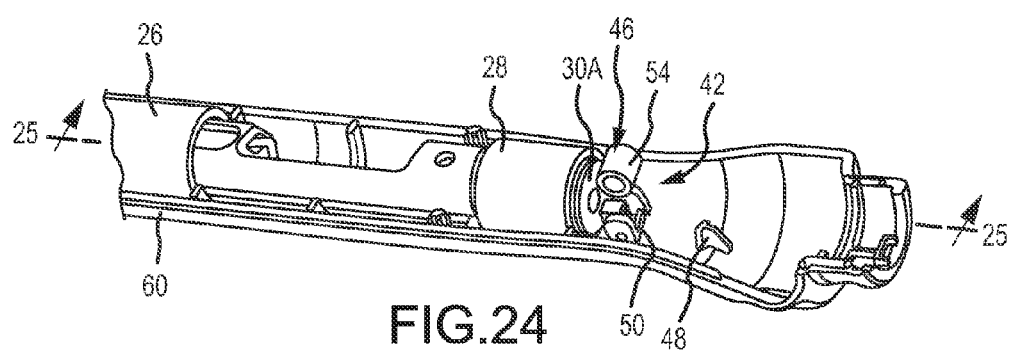
FIG. 24 is a fragmentary, isometric view of the plunger slidably mounted in the lower handle housing in the orientation also shown in FIGS. 11-14.
Figure 25:
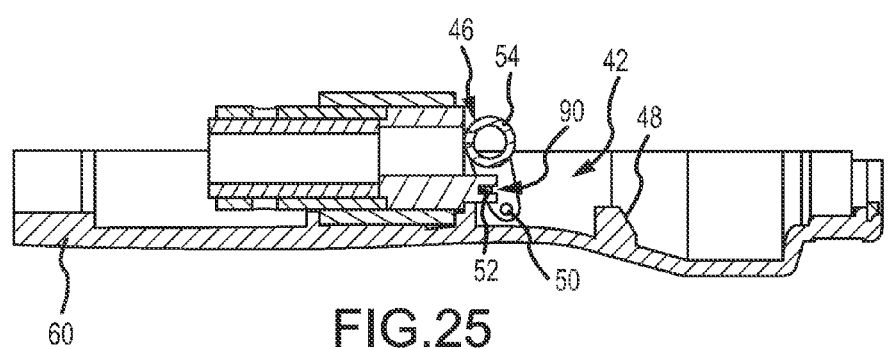
FIG. 25 is a fragmentary, cross-sectional view taken along ling 25-25 of FIG. 24, showing the plunger assembly mounted in the lower handle housing, with the active return-to-straight mechanism in an unactuated configuration.
Figure 26:
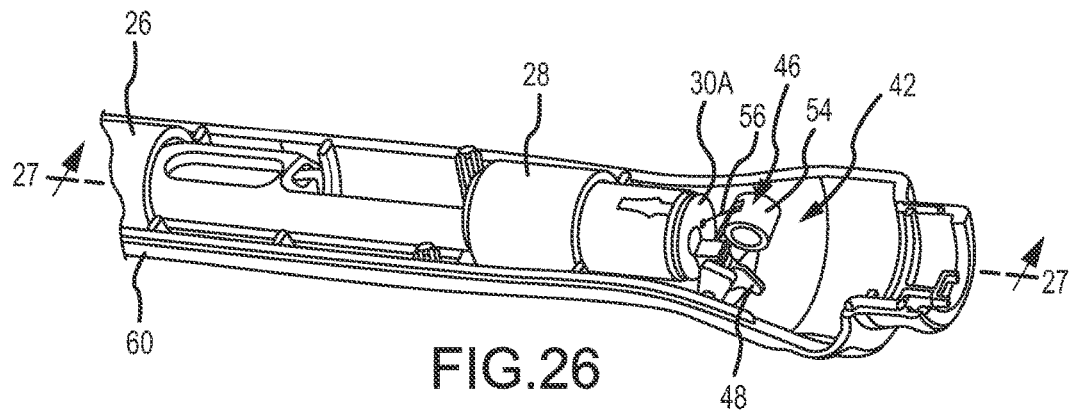
FIG. 26 is a fragmentary, isometric view similar to FIG. 24, but depicts the plunger assembly and the return-to-straight mechanism when the return-to-straight mechanism is actuated as also shown in FIGS. 18-21.
Figure 27:
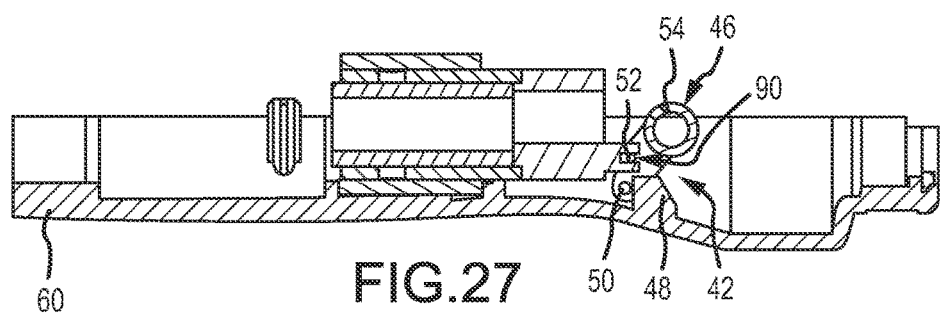
FIG. 27 is a fragmentary, cross-sectional view taken along line 27-27 of FIG. 26, showing the plunger assembly and the return-to-straight mechanism in the configuration also shown in FIG. 26.
Figure 28:
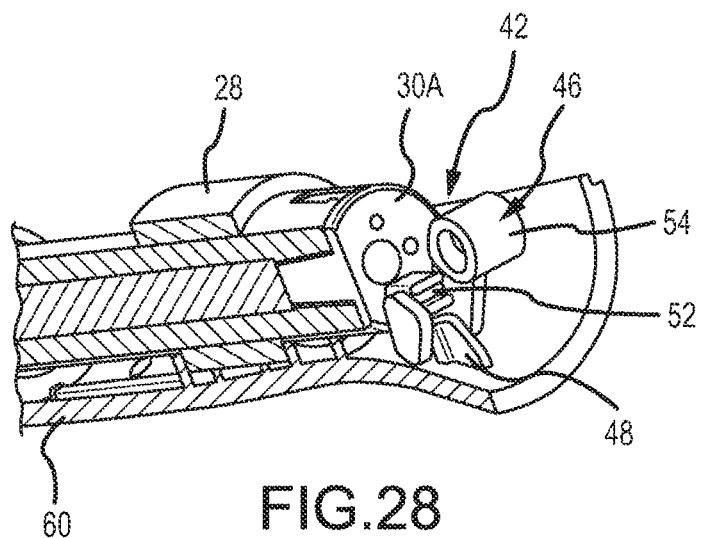
FIG. 28 is a fragmentary, isometric, cross-sectional view of the return-to-straight mechanism in its actuated configuration as also shown in, for example, FIGS. 26 and 27.

FIGS. 24-29 depict further details of the active return-to-straight mechanism 42 according to the first embodiment. FIGS. 24 and 25 show the lever 46 in its unactuated configuration. As shown to best advantage in FIG. 29, which is an isometric view of the first embodiment of the lever 46, separated away from remaining portions of the active return-to-straight mechanism, this lever includes a tuner drum 54, a pull wire tensioning arm 86, an activation pin or segment 50, a pin carrier segment 88, and a pivot pin 52. As shown in FIGS. 24-28, the lever 46, in this embodiment, is mounted to the plunger cap 30A by frictionally engaging the lever pivot pin 52 in a pin channel 90 extending proximally from the rear surface of the plunger cap 30A. FIGS. 25, 27, and 28 clearly show the pivot pin 52 in position in the pin channel 90.

Referring back to FIGS. 24 and 25, when the active return-to-straight mechanism 42 is in the unactuated configuration, a tuner drum 54 is close to or against the rear surface (i.e., the proximal surface) of the plunger cap 30A. When the return-to-straight mechanism is actuated, as shown to good advantage in FIGS. 26-28, the actuation boss 48 (part of the lower handle housing 60 in this embodiment) presses against the lever actuation segment 50, thereby pivoting the lever 46 proximally (i.e., rightward in FIGS. 26-28), which pulls on the inactive deflection element 56 (see, e.g., FIG. 26). Thus, as previously mentioned, in this configuration of the active return-to-straight mechanism 42, when the user pulls the plunger 12A back into the handle housing to its full-retracted or fully-neutral configuration, the active return-to-straight mechanism 42 is automatically actuated to tension the inactive deflection element 56, thereby pulling the distal deflectable section 16A of the catheter shaft 18A to its substantially straight configuration shown in, for example, FIGS. 18 and 20.

Figure 29:
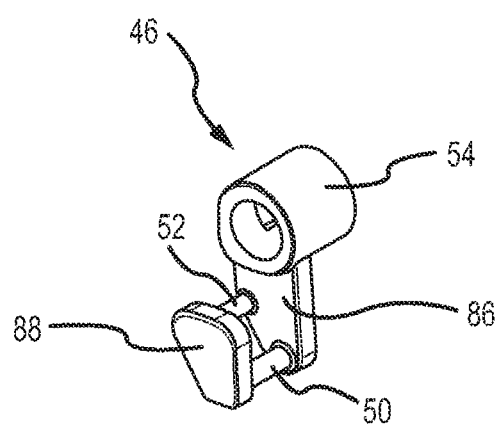
FIG. 29 is an isometric view of a lever comprising part of the return-to-straight mechanism depicted in, for example, FIGS. 12, 14, 16, 19, 21, 22, and 24-28.
Figure 30:
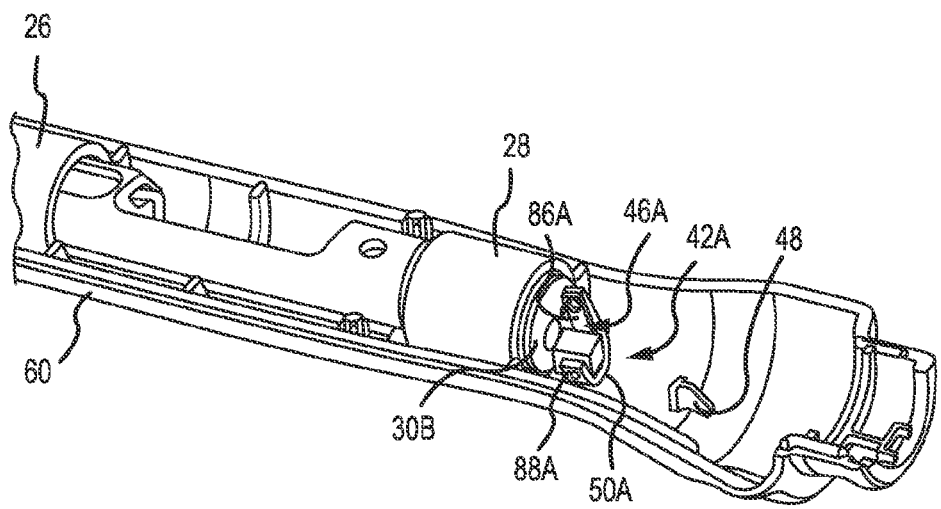
FIG. 30 is most similar to FIG. 24, but depicts an alternative lever comprising part of an alternative return-to-straight mechanism.
Figure 31:
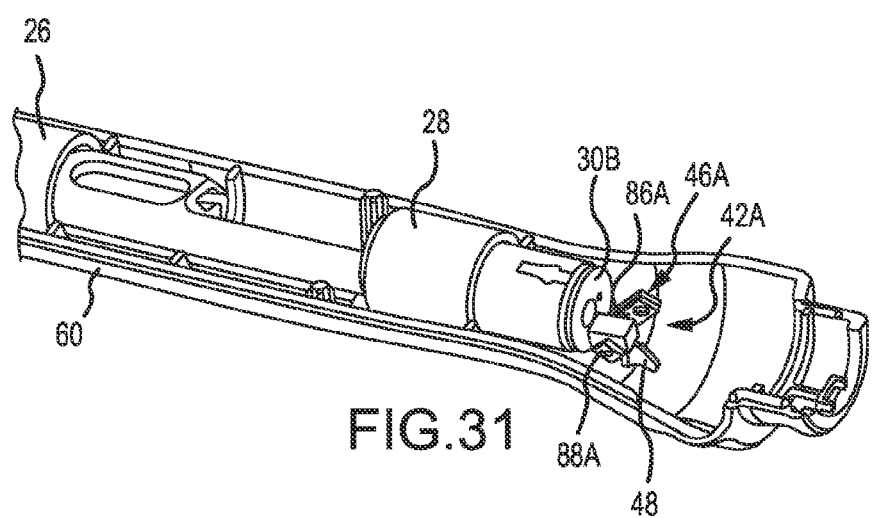
FIG. 31 is most similar to FIG. 26, but depicts the lever of FIG. 30 in an actuated configuration.
Figure 32:
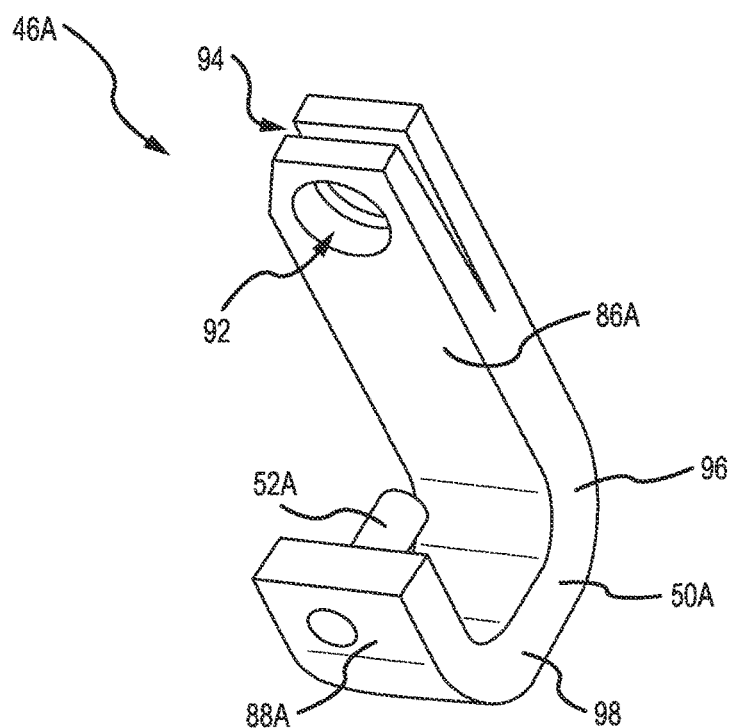
FIG. 32 is most similar to FIG. 29, but is an enlarged, isometric view of the alternative lever also depicted in FIGS. 30 and 31.

FIGS. 30-32 are similar to FIGS. 24, 26, and 29, respectively, but depict a lever 46A according to a second embodiment. As shown to best advantage in FIG. 32, the lever 46A according to this embodiment includes a tuner port 92, a pull wire slot 94, a pull wire tensioning arm 86A, a first elbow 96, an activation segment 50A, a second elbow 98, a pin carrier segment 88A, and a pivot pin 52A. When this lever 46A of this second embodiment of an active return-to-straight mechanism 42A is in its unactuated position, as shown to best advantage in FIG. 30, the pull wire tensioning arm 86A rests against or close to the rear surface of the plunger cap 30A. When the plunger assembly is fully retracted into the handle housing as shown in FIG. 31, the actuation boss 48 presses against the actuation segment 50A of the lever 46A, thereby driving the pull wire tensioning arm 86A away from the plunger cap 30B and thereby tensioning the inactive deflection element (not shown in FIGS. 31 and 32; but see inactive deflection element 56 in FIG. 26) to pull the distal deflectable section 16A of the catheter shaft 18A into the substantially straight configuration shown, for example, in FIG. 18.

FIGS. 33-43 depict an active return-to-straight mechanism 42B according to a third embodiment. In particular, FIGS. 33-36 depict the catheter 10B and various enlarged portions of the catheter while the catheter is in a fully-actuated configuration, placing the catheter tip portion 16A in a fully-deflected configuration. FIGS. 37-39 depict the catheter 10B, and enlarged portions of the catheter, when the plunger assembly 12B is in a semi-neutral position (i.e., a nearly fully-retracted configuration). Finally, FIGS. 40-43 depict the catheter 10B and various enlarged components of the catheter, when the plunger assembly 12B has been fully retracted to a neutral position (i.e., when the plunger assembly has been fully retracted into a handle housing 14C), thereby actuating the active return-to-straight mechanism 42B.

Figure 36:
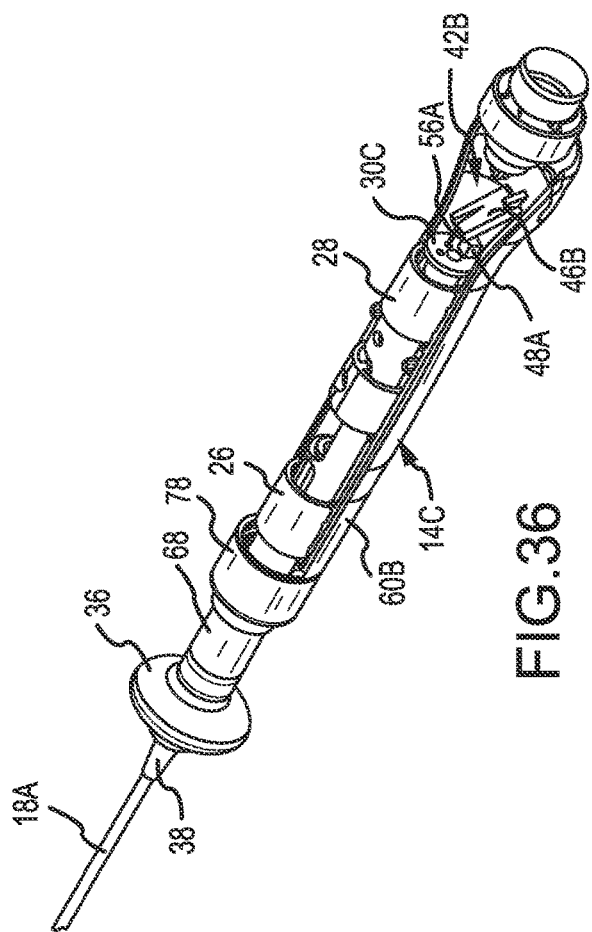
Figure 35:
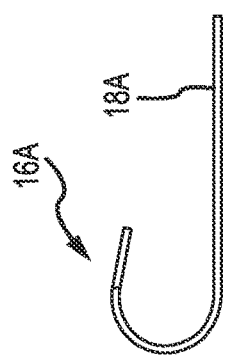

As shown to best advantage in FIGS. 34, 36, 38, 41, and 43, in this configuration, the active return-to-straight mechanism 42B includes a lever 46B that is pivotably mounted to the lower handle housing 60B, and an actuation boss 48A extends proximally from the proximal surface of the plunger cap 30C. When the steering actuator is fully actuated, as shown in FIGS. 33-36, the distal deflectable section 16A of the catheter shaft 18A is fully deflected, as best shown in FIGS. 33 and 35; and the actuation boss 48A is separated from the lever 46B as shown in FIGS. 34 and 36.

When the plunger assembly 12B is then retracted to a semi-neutral position (i.e., when the plunger assembly is partially retracted into the handle housing 14C), as shown in FIGS. 37-39, the actuation boss 48A makes initial contact with the lever 46B. In this configuration, the distal deflectable section 16A of the catheter shaft 18A has partially returned to the substantially straight configuration. In particular, the distal deflectable section 16A of the catheter shaft is no longer in the fully-deflected configuration shown in FIGS. 33 and 35. Rather, the distal deflectable section of the catheter shaft is in a partially-deflected configuration shown in FIGS. 37 and 39.

Figure 40:
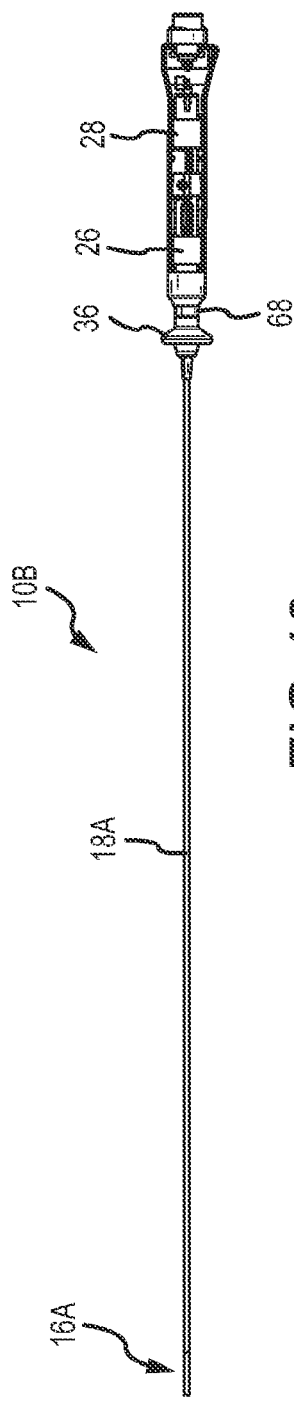
FIGS. 40-43 are similar to FIGS. 18-21, respectively, but depict the actuator shown to good advantage in FIGS. 34 and 36 when the plunger is in a neutral configuration (i.e., when the plunger is fully retraced into the handle housing), after the return-to-straight mechanism shown to good advantage in, for example, FIGS. 34 and 36 has been actuated.
Figure 41:
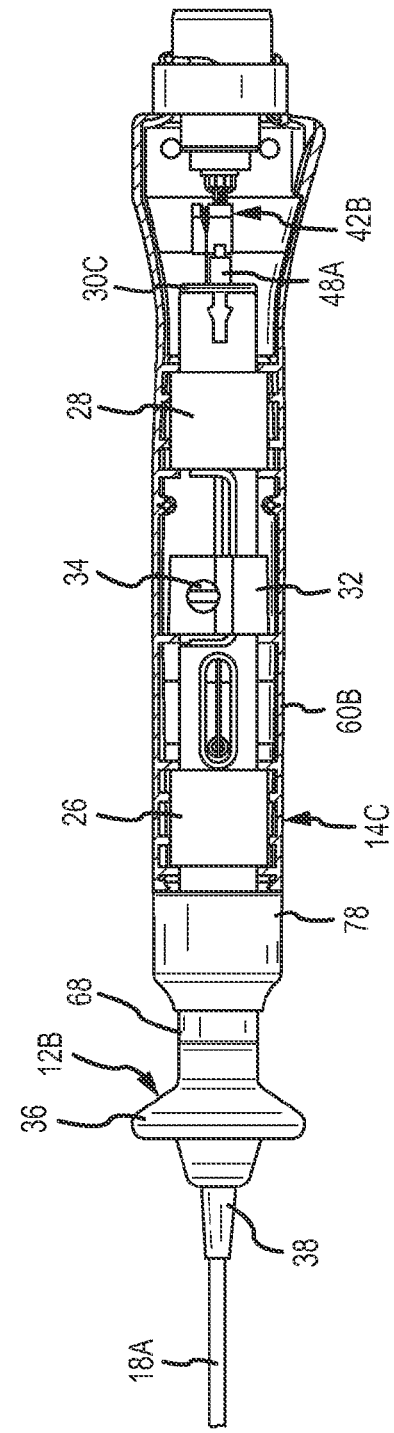
Figure 42:
Figure 43:
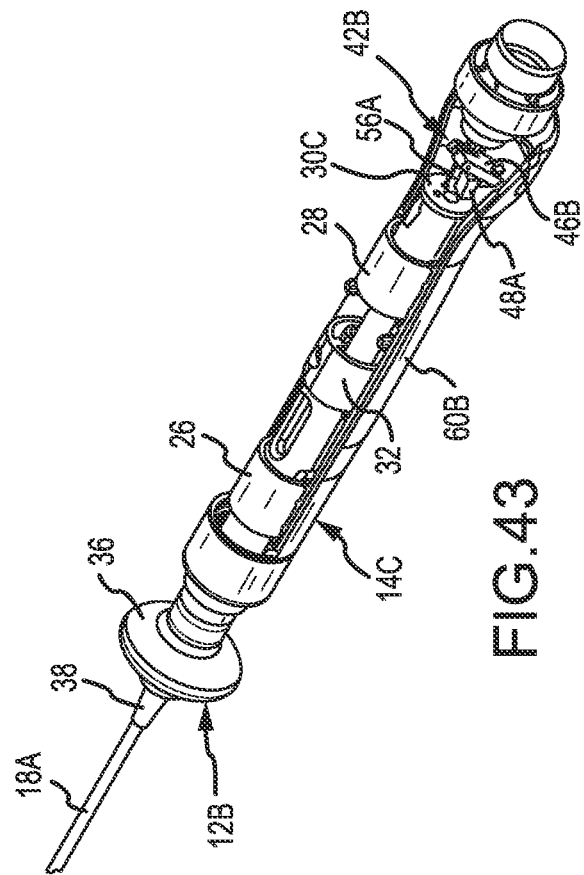

Referring next to FIGS. 40-43, when the plunger assembly 12B is subsequently returned to its neutral position (i.e., when the plunger assembly is fully retracted into the handle housing 14C as shown to the best advantage in FIGS. 41 and 43), the actuation boss 48A extending proximally from the plunger cap 30C presses the lever 46B proximally, which tensions the inactive deflection element 56A, which pulls the distal deflectable section 16A of the catheter shaft 18A into a substantially straight configuration shown in, for example, FIGS. 40 and 42.

In all of the active return-to-straight mechanisms described above in connection with FIGS. 11-43, the physician need only actuate a single mechanism to not only create a desired amount of shaft deflection, but also to fully return the catheter shaft to a substantially straight configuration.

Figure 44:
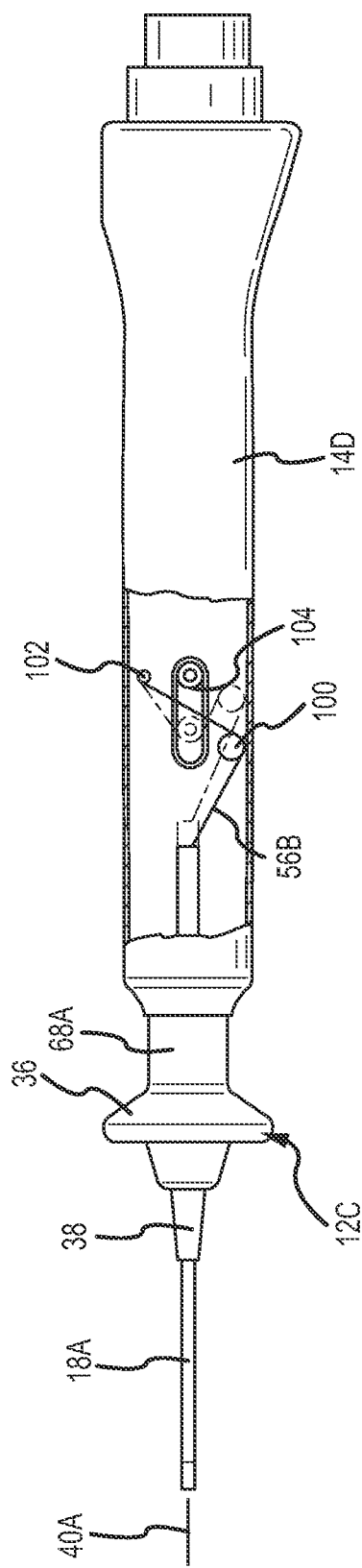
FIG. 44 is a fragmentary view of a catheter handle according to another embodiment having an active return-to-straight mechanism.

FIG. 44 depicts a fourth embodiment for actively returning the distal deflectable portion of a catheter shaft 18A to a substantially straight configuration through interaction with a single user actuator 116. In particular, FIG. 44 shows a plunger-type actuator 12C and a fragment of a catheter shaft 18A. In FIG. 44, a pull wire 56B (other than the pull wire used to deflect the distal deflectable section of the catheter shaft) is shown in solid lines extending around a wire lateral deflection pin 100 to a wire anchor 102. In this configuration, the lateral deflection pin 100 and the wire anchor 102 are located on opposite sides of the catheter longitudinal axis 40A, and the wire anchor is located proximal to the lateral deflection pin. A wire longitudinal deflection pin 104 is also shown in solid lines. This wire longitudinal deflection pin is mounted to the handle housing, whereas the lateral wire deflection pin 100 moves with the plunger assembly 12C.

Still referring to FIG. 44, in a first configuration, the plunger assembly is fully extended from a handle housing 14D, which would place the distal section of the catheter in a fully-deflected configuration similar to that shown in, for example, FIGS. 3, 13, and 35. When, on the other hand, the plunger is placed in its fully-retracted configuration, the pull wire would follow the path shown in dashed lines around the wire lateral deflection pin 100 (shown in FIG. 44 as a dashed circle) and the wire longitudinal deflection pin 104 (also shown in FIG. 44 as a dashed circle). As may be discerned from a review of FIG. 44, the wire path is longer when the plunger assembly is in its fully-retracted configuration then when the plunger assembly is in its fully-extended configuration. Thus, the depicted pull wire 56B is tensioned when the plunger assembly is in its fully-retracted configuration. This tensioning of the noted pull wire may be used to pull the distal deflectable section of the catheter shaft to a substantially straight configuration similar to that shown in, for example, FIGS. 18 and 40.

Figure 45:
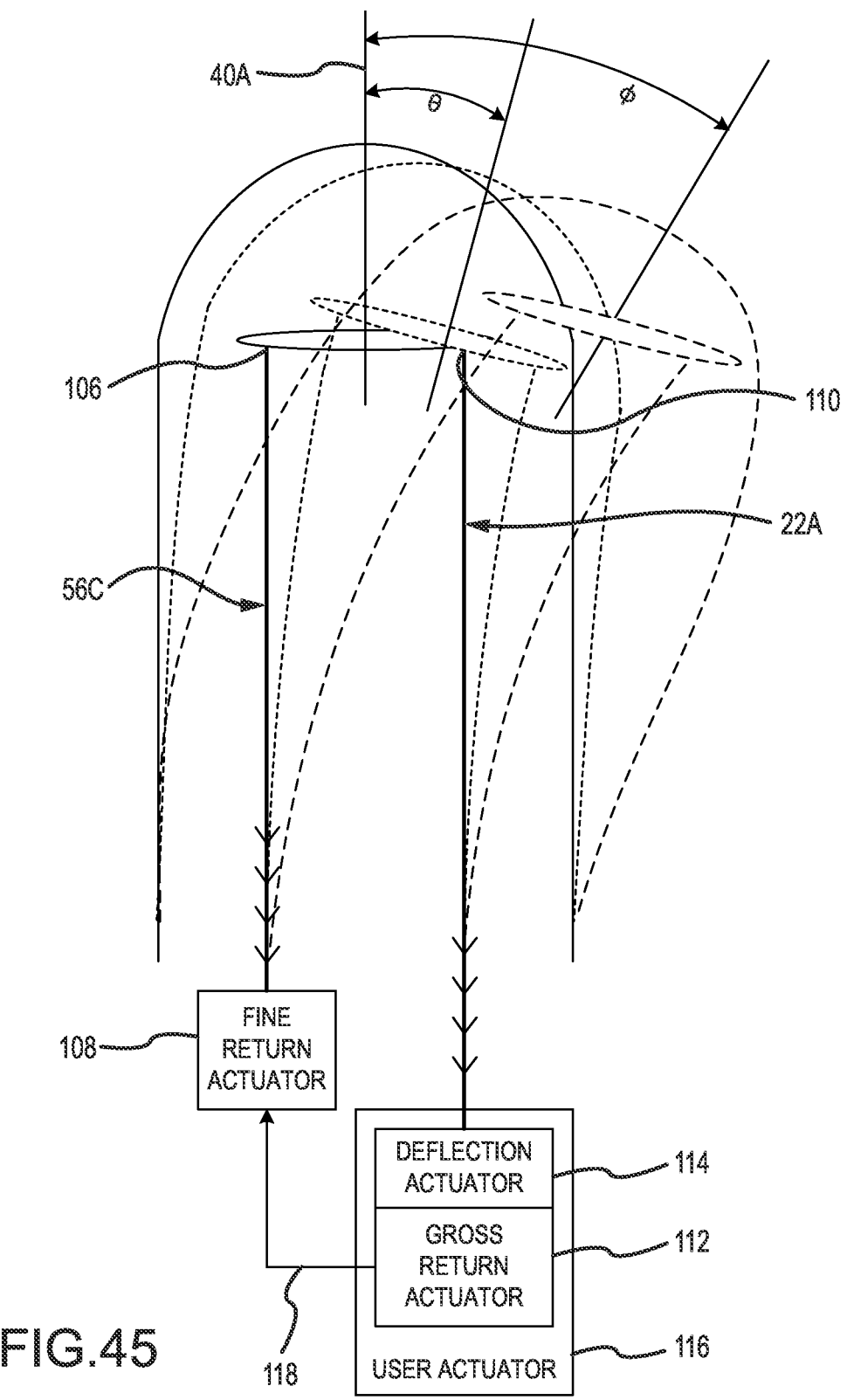
FIG. 45 is a schematic diagram showing the basic function of the return-to-straight mechanism according to some embodiments, wherein the primary or gross return actuator automatically triggers the secondary or fine return actuator.

FIG. 45 schematically depicts the distal deflectable section of the catheter shaft in a substantially-straight configuration (solid lines), in a partially-deflected configuration (lines created from short dashes), and in a hypothetical, fully-deflected configuration (lines created from long dashes). An inactive deflection element 56C is shown in solid lines extending from a first anchor point or connection 106 (located distal on the catheter shaft) to a secondary or fine return actuator 108. Similarly, an active deflection element 22A is shown extending from a second anchor point or connection 110 (located distal on the catheter shaft) to a primary or gross return actuator 112 comprising part of a deflection actuator 114, both of which a user activates via the user actuator 116. Although the anchor points 106, 110 are depicted for simplicity in FIG. 45 as being located at the same longitudinal position along the catheter shaft, these deflection elements need not be coupled or attached at the same distal location or to the same pull ring or other anchor points. Also, each anchor point 106,110 that is schematically represented in FIG. 45 could be, for example, a location where a pull wire is attached (e.g., by crimping or welding) to, for example, a pull ring mounted or formed in a distal portion of a catheter shaft.

As also shown in FIG. 45, the fine return actuator 108 is automatically and directly triggered by the gross return actuator 112. This is schematically represented in this figure by the "Trigger" line 118 connecting the "gross return actuator" box 112 to the "fine return actuator" box 108. This schematically represents what occurs in the embodiments shown in, for example, FIGS. 11-43. When the deflection actuator is fully actuated, the distal deflectable section of the catheter is deflected by the angle phi ($\Phi$) from the longitudinal axis 40A of the substantially straight catheter. This angle may be selected to meet the needs of the physician, but it is depicted in FIG. 45 as being approximately 45 degrees. This angle phi ($\Phi$) also corresponds to the angle phi ($\Phi$) shown in, for example, FIG. 3.

As also shown in FIG. 45, when the deflection actuator 114, acting as a gross return actuator 112, is returned to its neutral position, the catheter shaft may not return to its fully-straight configuration. Rather, the catheter shaft may remain slightly offset from straight by an angle theta ($\theta$). Then, in order to return the distal deflectable section of the catheter shaft to its fully-straight or substantially-straight configuration, a secondary or fine return actuator 108 may be actuated. As mentioned, in the configuration schematically depicted in FIG. 45, the fine return actuator 108 is automatically triggered by the gross return actuator 112 being returned to its neutral position.

Figure 46:
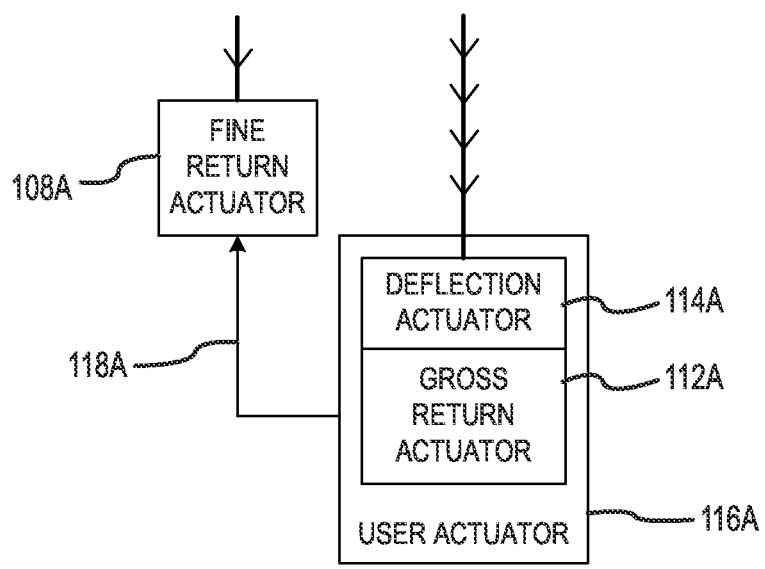
FIG. 46 is a fragmentary view of a portion of FIG. 45, representing embodiments where the primary or gross return actuator does not directly trigger the secondary or fine return actuator.
Figure 51:
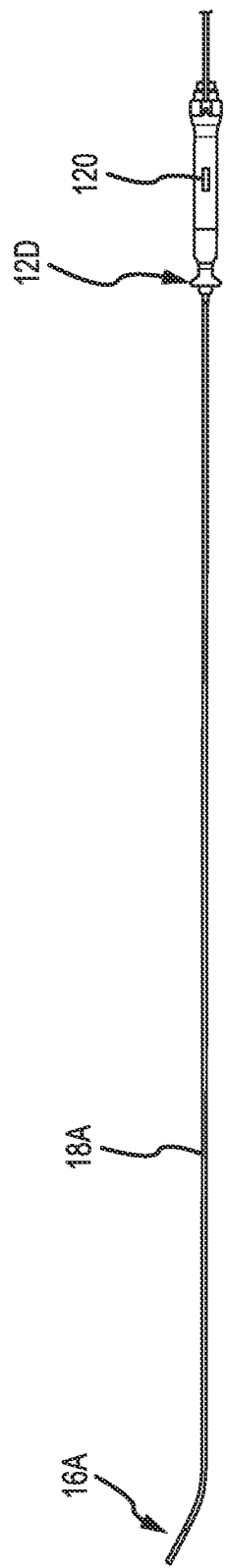
Figure 52:
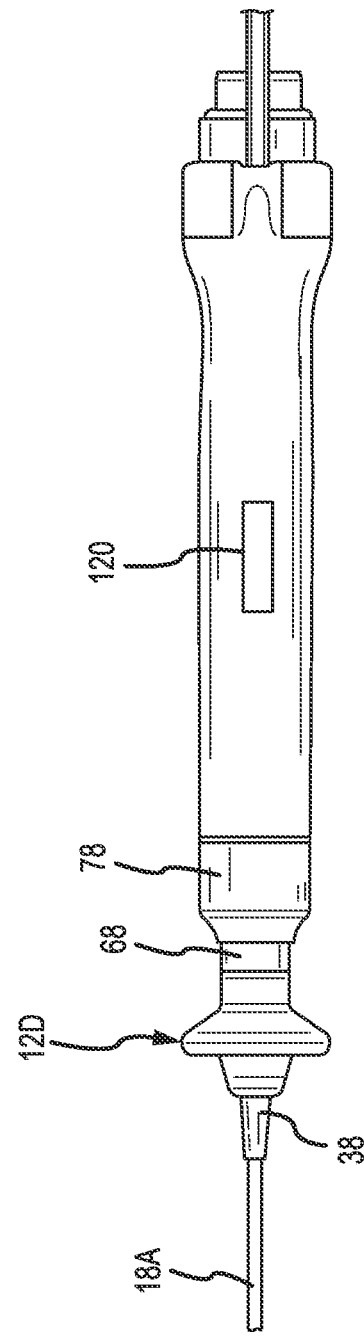

FIG. 46 is similar to FIG. 45, but schematically represents embodiments where the fine return actuator 108A is actuated by the user, but not necessarily directly by the gross return actuator 112A. The embodiment depicted in FIG. 44 behaves in the manner depicted in FIG. 46. Still other manners of initiating the fine return actuator are contemplated by the present disclosure, such as, for example, using a sensor or sensors (not shown) to detect a position of the gross return actuator and/or user actuator, and triggering the fine return actuator when the sensed position indicates that the gross return actuator and/or user actuator has exhausted or sufficiently slowed its ability to continue returning the catheter towards its neutral position. For example, a sensor could be located in the handle cap (see, for example, element 78 in FIG. 48) that could sense the position of the plunger body (see, for example, element 68 in FIG. 48) via, for example, a sensible feature mounted in or on the plunger body.

Referring next to FIGS. 47-58, an active return-to-straight mechanism according to another embodiment and comprising multiple user actuators is described next. In FIGS. 47-50, the primary actuator 12D has been fully actuated, thereby placing the deflectable distal section 16A of the catheter shaft 18A in a fully-deflected configuration shown to best advantage in FIGS. 47 and 49. When the primary actuator 12D is in this fully-actuated configuration, the thumb boss 36 has been pushed distally, separating the thumb boss from the handle cap 78 as shown to good advantage in FIGS. 48 and 50. As also depicted in FIGS. 48 and 50, a secondary, manual return-to-straight slider 120 is in its 'off' or unactuated position.

In FIGS. 51-54, the primary actuator 12D has been returned to a neutral position (fully-retracted position), but the secondary, manual, return-to-straight slider 120 remains in the 'off' position. Thus, the catheter distal deflectable section 16A remains in a slightly-deflected configuration as shown to good advantage in FIGS. 51 and 53. Comparing FIG. 52 to FIG. 48, or FIG. 54 to FIG. 50, it is apparent that the plunger assembly 12D has been retracted in FIGS. 52 and 54.

In FIGS. 55-58, the plunger assembly 12D remains in the same neutral configuration shown in FIGS. 51-54. However, in the configuration shown in FIGS. 55-58, the secondary, manual return-to-straight slider 120 has been actuated (i.e., pulled proximally to the 'on' position), thereby pulling the catheter tip portion 16A to a substantially-straight configuration shown to good advantage in FIGS. 55 and 57. This return-to-straight mechanism achieves some of the advantages previously described, but requires activation of a second actuator.

Figure 59:
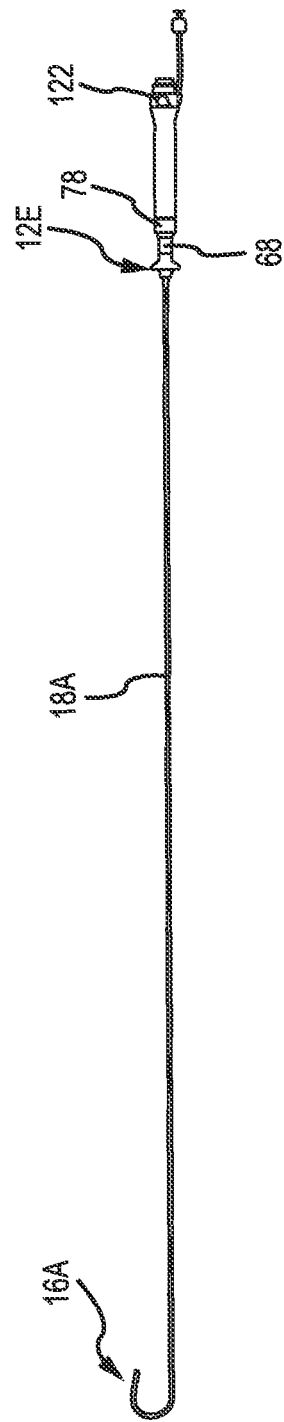
FIGS. 59-62 are most similar to FIGS. 47-50, respectively, but depict an alternative, second, manual actuator in an unactuated configuration.
Figure 60:
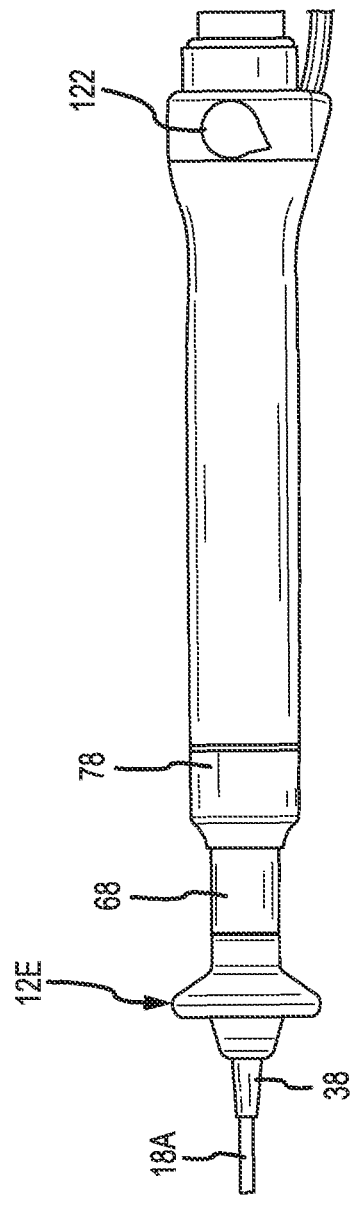
Figure 61:
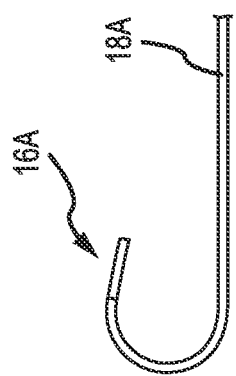
Figure 62:
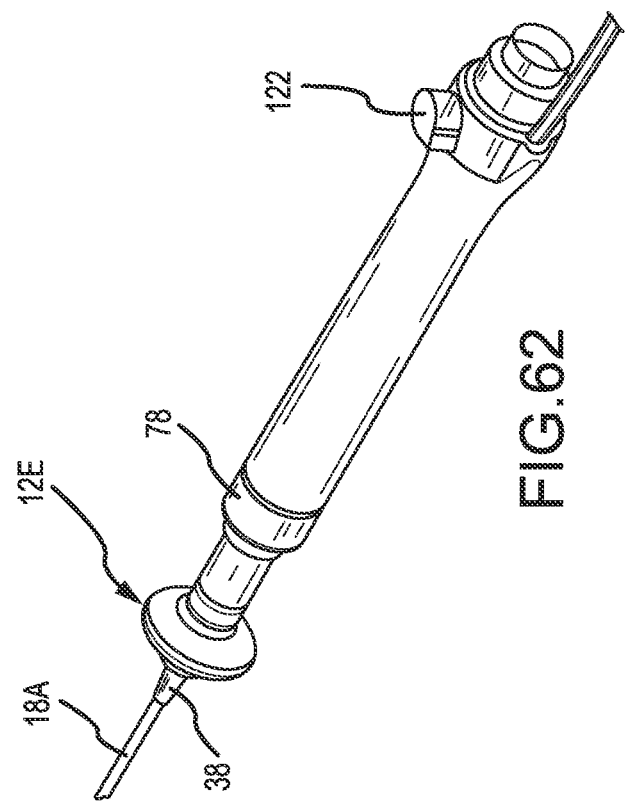

FIGS. 59-70 are similar to FIGS. 47-58, respectively, but disclose a different embodiment of an active return-to-straight mechanism. In FIGS. 59-62, the primary actuator 12E is in a fully-actuated configuration, which pulls the distal deflectable section 16A of the catheter shaft 18A into its fully-deflected configuration shown in FIGS. 59-62. FIGS. 59, 60, and 62 show the plunger assembly 12E (i.e., the primary actuator) in its fully-extended configuration, which results in the fully-deflected distal tip 16A section shown in FIGS. 59 and 61.

Figure 63:
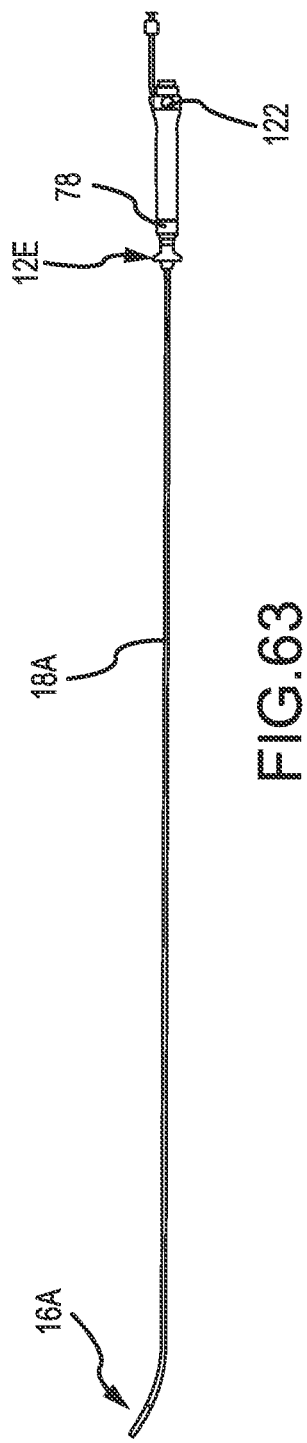
Figure 64:
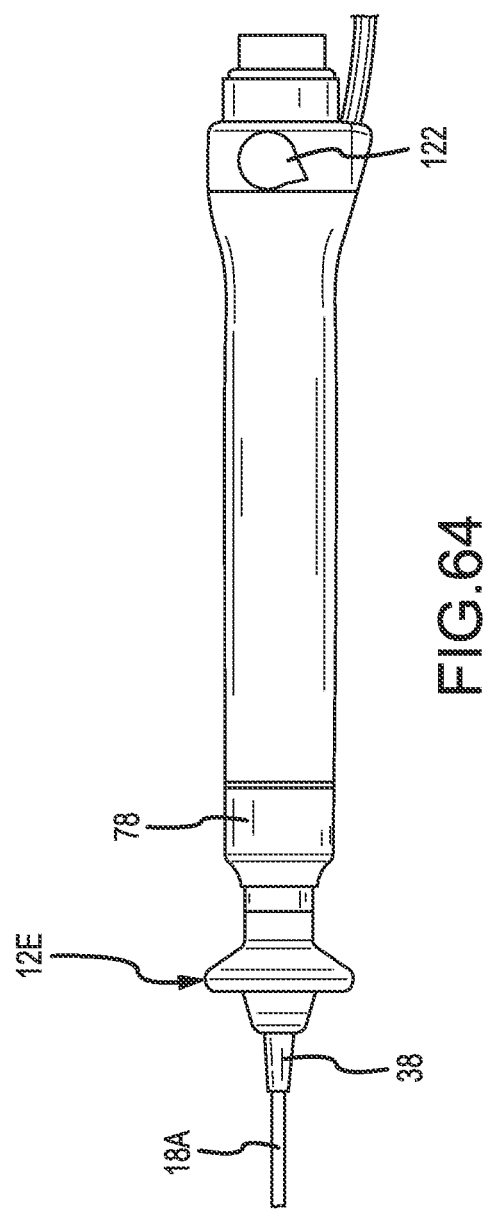
Figure 67:
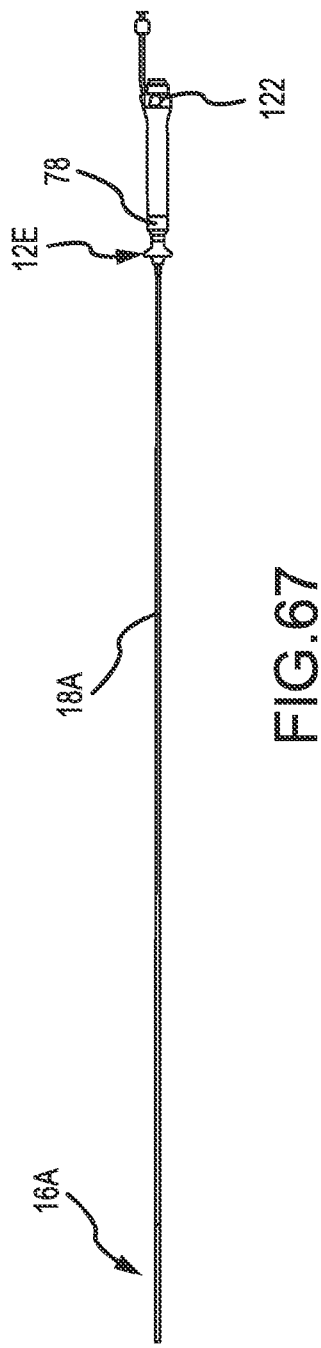
Figure 68:
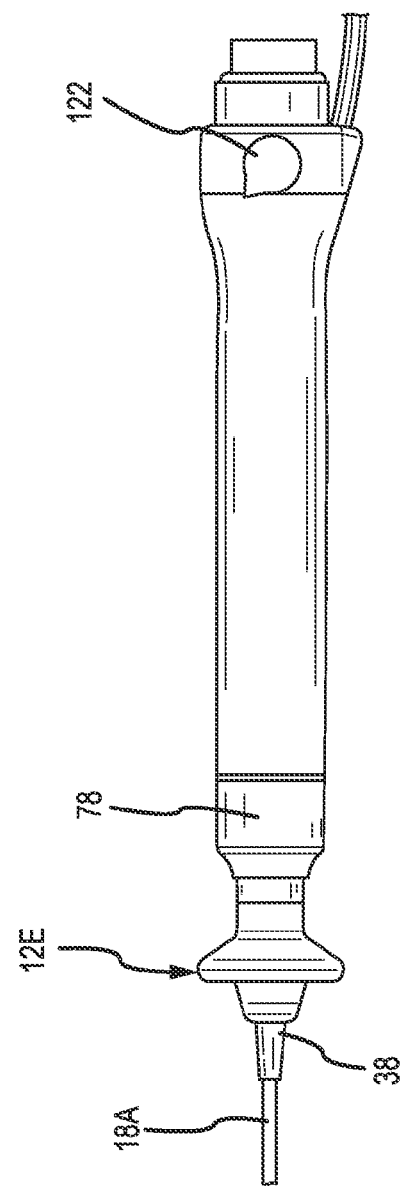

In FIGS. 63-66, the plunger assembly 12E has been returned to a neutral position (i.e., the plunger assembly has been fully retracted into the handle housing). The secondary actuator 122, which is the manual, return-to-straight knob 122, remains in the 'off' position. That is, comparing FIG. 64 to FIG. 60, or FIG. 66 to FIG. 62, it is possible to see that the manual, return-to-straight knob remains in the 'off' position despite the fact that the plunger assembly has been moved from its fully-actuated configuration to its neutral position. Despite the fact that the plunger assembly is in its neutral position, the distal deflectable section 16A of the catheter shaft may remain in a slightly-deflected configuration as shown in FIGS. 63 and 65. Upon manually activating the return-to-straight mechanism to the 'on' position represented in FIGS. 68 and 70, the inactive deflection element is tensioned, thereby pulling the distal section 16A of catheter shaft 18A to the substantially-straight configuration shown to best advantage in FIGS. 67 and 69.

Catheter manufactures may make a single catheter shaft for use on both bi-directional and uni-directional catheters. This may, for example, simplify manufacturing processes and inventory. Such 'dual-use' catheter shafts may include two deflection elements or pull wires. In a bi-directional catheter, both deflection elements are active. In a uni-directional catheter, such as the uni-directional catheters depicted and described throughout this disclosure, only one of the deflection elements may be active. However, in the embodiments described herein, the presence of the inactive deflection element is leveraged to actively return the distal deflectable catheter shaft section to a substantially straight configuration during a medical procedure.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of all embodiments.

Reference throughout the specification to "various embodiments," "some embodiments," "one embodiment," or "an embodiment," or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial or directional terms such as "vertical," "horizontal," "up," "down," "clockwise," and "counter-clockwise" may be used herein with respect to the illustrated embodiments. However, medical instruments may be used in many orientations and positions, and these terms are not intended to be limiting and absolute.

Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relation to each other. As used herein, joinder references may also include two components that are molded as a single or unitary piece. Changes in detail or structure may be made without departing from the spirit of the invention as defined in the appended claims.

What is claimed is:

1. A deflectable catheter comprising the following:
   a catheter shaft comprising the following:
      a shaft proximal end,
      a shaft distal end,
      a shaft deflectable distal portion, and
      first and second tension members extending from the shaft proximal end to the shaft deflectable distal portion;
   a deflection actuator operatively coupled to the first and second tension members and configured to cause deflection of the deflectable distal portion from an initial configuration, wherein the deflection actuator comprises an active return-to-straight mechanism comprising (i) a primary return actuator configured to partially reverse the deflection of the deflectable distal portion and (ii) a secondary return actuator configured to continue reversing the deflection of the deflectable distal portion towards the initial configuration, wherein the primary return actuator is configured to automatically and directly trigger the secondary return actuator; and
   a handle housing, wherein the deflection actuator is at least partially mounted in the handle housing.

2. The deflectable catheter of claim 1, wherein the primary return actuator is operatively coupled to the first tension member, and the secondary return actuator is operatively coupled to the second tension member.

3. The deflectable catheter of claim 2, wherein the secondary return actuator comprises a lever and an actuation boss, wherein the actuation boss is configured to actuate the lever from an unactuated configuration to an actuated configuration, and wherein the lever is adapted to tension the second tension member when the lever is actuated.

4. The deflectable catheter of claim 2, wherein the secondary return actuator comprises a lever and an activation boss.

5. The deflectable catheter of claim 4, wherein the lever is pivotally mounted on the primary return actuator, and wherein the actuation boss is affixed to the handle housing.

6. The deflectable catheter of claim 4, wherein the lever is mounted for movement relative to the primary return actuator, and wherein the actuation boss is affixed to the handle housing.

7. The deflectable catheter of claim 4, wherein the lever is pivotally mounted on the handle housing, and wherein the actuation boss is affixed to the primary return actuator.

8. The deflectable catheter of claim 4, wherein the lever is mounted for movement relative to the handle housing, and wherein the actuation boss is affixed to the primary return actuator.

9. The deflectable catheter of claim 4, wherein the lever is attached to the second tension member via a tuner and a tuner drum.

10. The deflectable catheter of claim 1, wherein the deflection actuator is operable to variably deflect the shaft deflectable distal portion to a predetermined maximum deflection angle relative to a shaft longitudinal axis extending between the shaft proximal end and a deflection commencement point located at a proximal end of the shaft deflectable distal portion; wherein the primary return actuator is operable to variably return the shaft deflectable distal portion to an offset angle relative to the shaft longitudinal axis, the offset angle being less than the predetermined maximum deflection angle; and wherein the secondary return actuator is operable to variably return the shaft deflectable distal portion from the offset angle and into alignment with the shaft longitudinal axis.

11. The deflectable catheter of claim 1, wherein said deflection actuator comprises a plunger assembly that is slidably supported by at least one sleeve bearing mounted to the handle housing, wherein the secondary return actuator comprises a lever and an activation boss, and wherein the lever is pivotably mounted to a proximal end of the plunger assembly.

12. The deflectable catheter of claim 1,
wherein the deflection actuator is adapted to be variably actuated between
(A) a neutral configuration wherein the deflection actuator is not actively deflecting the shaft deflectable distal portion, and
(B) a fully-actuated configuration wherein the deflection actuator is actively deflecting the shaft deflectable distal portion to a maximum set deflection angle; and
wherein the active return-to-straight mechanism is adapted to be automatically actuated to place the shaft deflectable distal portion in a substantially straight configuration as the deflection actuator is returned to the neutral configuration.

13. The deflectable catheter of claim 1, wherein the secondary return actuator comprises a pin affixed to the handle housing and configured to alter a path length of the second tension member.

14. The deflectable catheter of claim 1, wherein the primary return actuator is coupled to the secondary return actuator, and wherein the secondary return actuator is configured to continue reversing the deflection of the distal portion of the catheter shaft in response to the primary return actuator reaching a positional threshold.

15. The deflectable catheter of claim 1, wherein the primary return actuator and the secondary return actuator are commonly embodied on a plunger device.

* * * * *